(12) United States Patent
Kawano et al.

(10) Patent No.: US 8,731,637 B2
(45) Date of Patent: May 20, 2014

(54) INTRA-SUBJECT MEDICAL SYSTEM, METHOD OF OPERATING BODY-INSERTABLE APPARATUS AND OPERATIVE TREATMENT

(75) Inventors: Hironao Kawano, Hino (JP); Hironobu Takizawa, Hachioji (JP); Akio Uchiyama, Yokohama (JP); Atsushi Chiba, Hachioji (JP); Takeshi Yokoi, Hino (JP); Hideo Ito, Akishima (JP); Hidetake Segawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1574 days.

(21) Appl. No.: 11/655,318

(22) Filed: Jan. 19, 2007

(65) Prior Publication Data

US 2007/0191671 A1 Aug. 16, 2007

(30) Foreign Application Priority Data

Jan. 19, 2006 (JP) ................................. 2006-011566

(51) Int. Cl.
*A61B 5/05* (2006.01)
(52) U.S. Cl.
USPC ............ 600/417; 128/899; 600/109; 600/118
(58) Field of Classification Search
USPC ......... 600/9–14, 114, 117, 118, 160; 128/899
See application file for complete search history.

(56) References Cited

U.S. PATENT DOCUMENTS

| | | | |
|---|---|---|---|
| 4,278,077 A | 7/1981 | Mizumoto | |
| 5,681,260 A * | 10/1997 | Ueda et al. | 600/114 |
| 6,770,022 B2 * | 8/2004 | Mechlenburg et al. | 600/9 |
| 2004/0111011 A1 * | 6/2004 | Uchiyama et al. | 600/160 |
| 2004/0127787 A1 * | 7/2004 | Dimmer et al. | 600/424 |
| 2004/0254455 A1 | 12/2004 | Iddan | |
| 2005/0159637 A9 * | 7/2005 | Nelson et al. | 600/12 |
| 2005/0216231 A1 | 9/2005 | Aoki et al. | |

FOREIGN PATENT DOCUMENTS

| | | |
|---|---|---|
| EP | 0 957 369 A1 | 11/1999 |
| EP | 1 510 169 A1 | 3/2005 |
| GB | 2 287 275 A | 9/1995 |
| JP | 55-19124 | 2/1980 |

(Continued)

OTHER PUBLICATIONS

Extended Supplementary European Search Report dated Dec. 18, 2009.

(Continued)

*Primary Examiner* — Charles A Marmor, II
*Assistant Examiner* — Carrie R Dorna
(74) *Attorney, Agent, or Firm* — Scully, Scott, Murphy & Presser, P.C.

(57) ABSTRACT

Provided is an intra-subject medical system which includes a body-insertable device and a physical quantity generator. The body-insertable device is to be introduced into a subject, is covered by a capsule-shaped exterior member, and includes a physical quantity detecting member which has a directivity to detect a predetermined physical quantity; at least one functional member which has a necessary function for examining or treating inside the subject; and a switch control unit which controls an on/off state or operation mode of the at least one functional member when the physical quantity detecting member detects a physical quantity. The physical quantity generator has a physical quantity emitting unit which emits a temporary physical quantity inside the subject; and a physical quantity direction changing unit which changes an emission direction of the physical quantity.

26 Claims, 42 Drawing Sheets

(56) References Cited

FOREIGN PATENT DOCUMENTS

| JP | 57-187506 | 11/1982 |
| JP | SHO 57-187506 | 11/1982 |
| JP | 9-143053 | 6/1997 |
| JP | 2849131 | 11/1998 |
| JP | 2004-117227 | 4/2004 |
| JP | 2004-261240 | 9/2004 |
| JP | 2005-73934 | 3/2005 |
| WO | WO 2004/086434 A2 | 10/2004 |

OTHER PUBLICATIONS

Abstract of Japanese Publication No. 02-224650, published Sep. 6, 1990.
U.S. Office Action dated Jun. 26, 2013 in related U.S. Appl. No. 13/408,322.

* cited by examiner

DATA PROCESSING/
CONTROL UNIT

IN USE          NOT IN USE

NOT IN USE          IN USE

IN USE          NOT IN USE

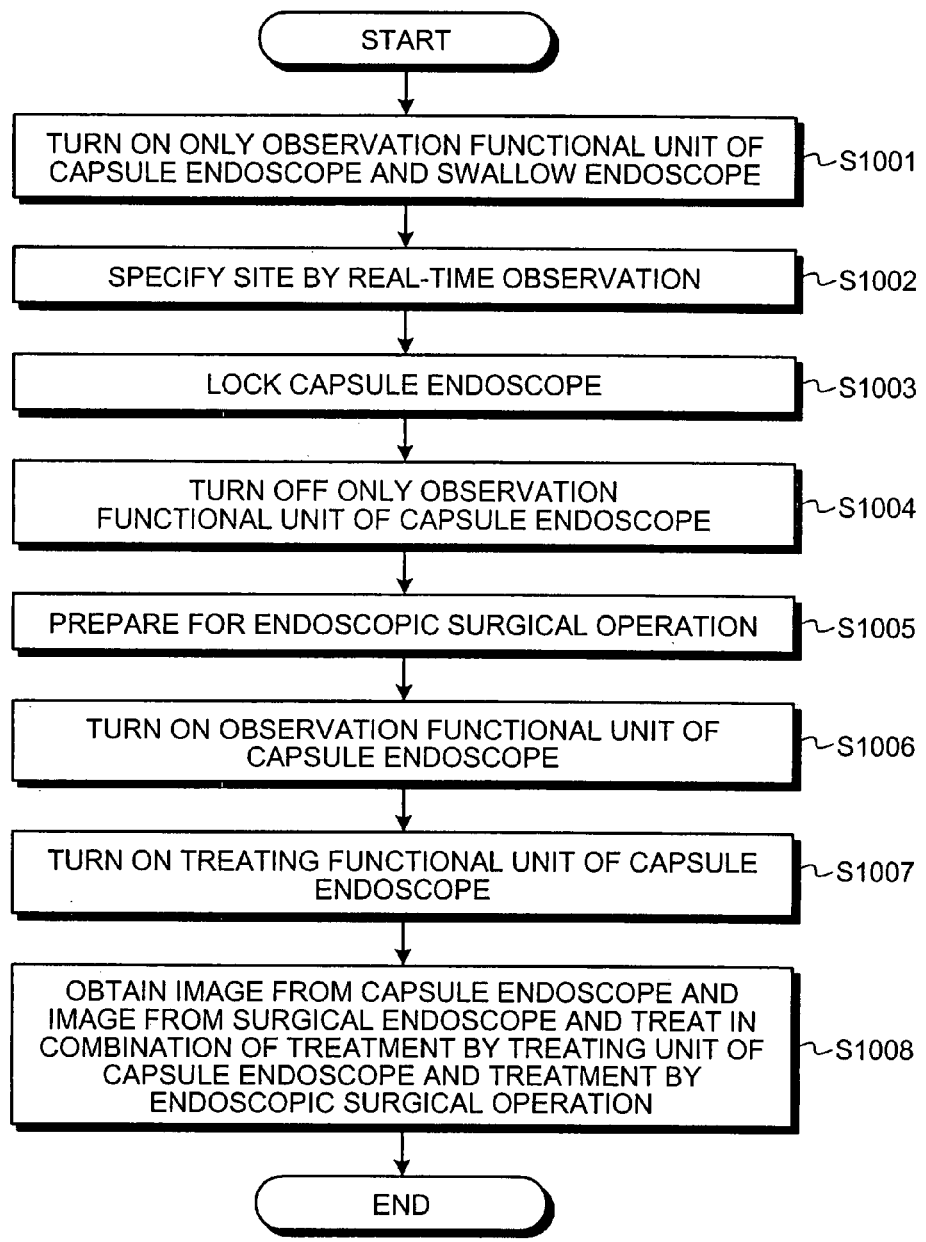

INTRA-SUBJECT MEDICAL SYSTEM, METHOD OF OPERATING BODY-INSERTABLE APPARATUS AND OPERATIVE TREATMENT

CROSS-REFERENCE TO RELATED APPLICATIONS

This application is based upon and claims the benefit of priority from Japanese Patent Application No. 2006-011566, filed Jan. 19, 2006, the entire contents of which are incorporated herein by reference.

BACKGROUND OF THE INVENTION

1. Field of the Invention

The present invention relates to an intra-subject medical system which performs various medical practices including examination or treatment in a body cavity in a subject, a method of operating body-insertable apparatus, and an operative treatment.

2. Description of the Related Art

Recently, in a field of endoscopes, a swallowed-type capsule endoscope has been introduced. In such a capsule endoscope, an imaging function and a radio communication function are provided. The capsule endoscope has a function for moving along with peristaltic movement in a body cavity in an internal organ such as the stomach and small intestine and sequentially taking images until it is naturally discharged from the human body, after swallowed by a patient though his or her mouth for the observation (examination).

As moving in the body cavity, data of images taken by the capsule endoscope in the human body is sequentially sent to outside by radio communication and stored in a memory provided in an external receiver. If the receiver including the radio communication function and memory function is carried by the patient, he or she may move freely even after swallowing the capsule endoscope and before discharging the capsule endoscope. After that, a doctor or a nurse may give a diagnosis by displaying the image of the internal organ based on the image data stored in the memory.

The above-described capsule endoscope is made in a small size and a limited power source is employed. Since the electricity consumption needs to be minimized, a system in which the on/off states of various functions in the capsule endoscope can be switched after the capsule endoscope is introduced into a subject is disclosed in, for example, Japanese Patent No. 2849131, Japanese Patent Application Laid-Open No. 2004-261240, and Japanese Patent Application Laid-Open No. 2005-73934. This turning on/off of each function is done by emitting a physical quantity such as a magnetic field from outside and detecting the physical quantity by a physical quantity detecting sensor provided in the capsule endoscope, as disclosed in, for example, Japanese Patent Application Laid-Open No. 9-143053 and Japanese Utility Model Application Laid-Open No. 57-187506.

However, there has been a problem that on/off states of the various functions can not be surely switched, since the physical quantity detecting sensor provided in the conventional capsule endoscope has directivity.

Further, there has been a problem that the physical quantity detecting sensor of a magnetism switch or the like cannot switch an on/off states of each function unless a physical quantity is kept being applied from outside of the subject so that it is difficult to maintain the on-state of the off-state securely.

SUMMARY OF THE INVENTION

At least one object of the present invention is to solve the problems.

An intra-subject medical system according to the present invention comprises a body-insertable device to be introduced into a subject, the body-insertable device being covered by a capsule-shaped exterior member and including a physical quantity detecting member which has a directivity to detect a predetermined physical quantity; at least one functional member which has a necessary function for examining or treating inside the subject; and a switch control unit which controls an on/off states or operation mode of the at least one functional member according to a detection result of physical quantity by the physical detecting member; a physical quantity generator having a physical quantity emitting unit which emits a temporary physical quantity inside the subject; and a physical quantity direction changing unit which changes an emission direction of the physical quantity.

A method of operating a body-insertable device according to the present invention comprises a swallowing step in which a subject swallows a body-insertable device with a function switch, in an off-state, for switching the on/off states of each functional member including an observing member in the body-insertable device; a switch-on step of turning on the function switch of the body-insertable device; and a control step of determining whether or not the body-insertable device has reached a desired specific site based on an image taken by the body-insertable device, repeating the procedure of determining whether or not the device has reached the desired specific site by keeping the function switch on when the device has not reached the desired particular site, and turning off the function switch when the device has reached the desired specific site.

A method of operating a body-insertable device according to the present invention comprises a swallowing step in which a subject swallows the body-insertable device; a moving step of moving the subject from a far position to a closer position to a magnet; and an on/off state control step of turning on a magnetic sensor in the body-insertable device and off a function in the body-insertable device by a magnetism of the magnet.

An operative treatment according to the present invention comprises a swallowing step in which a subject swallows a body-insertable device with a function switch, in an on-state, for turning on or off functions of various functional members including an observing member in the body-insertable device; an observing step of observing inside of the subject in real time with an observing function of the observing member to specify a desired site; a switch-off step of turning off the function switch when the desired site is specified in the observing step; an administration step of administering a peristalsis depressant to the subject; a preparing step of preparing for an endoscopic surgical operation; a switch-on step of turning on the function switch; and a treating step of treating the desired site with reference to an image from the observing member and an image from a surgical endoscope used in an endoscopic surgical operation.

An operative treatment according to the present invention comprises a swallowing step in which a subject swallows a body-insertable device with a function switch, in an on-state, of an observing member among function switches for turning on or off functions of various functional members including the observing member in the body-insertable device; an observing step of observing inside of the subject in real time with an observing function of the observing member to specify a desired site; a locking step of, when the desired site is specified in the observing step, turning on the function switch of a locking member to lock the body-insertable device; a switch-off step of turning off the function switch of the observing member; a preparing step of preparing for an endoscopic surgical operation; a switch on step of turning on the function switch of the observing member; and a treating step of treating the desired site with reference to an image from the observing member and an image from a surgical endoscope used in an endoscopic surgical operation.

An operative treatment according to the present invention comprises a swallowing step in which a subject swallows a body-insertable device with a function switch, in an off-state, for turning on or off functions of various functional members including an observing member in the body-insertable device; a guiding step of guiding the body-insertable device to a desired site with a rotational magnetic field while detecting the position of the body-insertable device; a preparing step of preparing for an endoscopic surgical operation; a switch-on step of turning on the function switch; and a treating step of treating the desired site with reference to an image from the observing member and an image from a surgical endoscope used in an endoscopic surgical operation.

An operative treatment according to the present invention comprises a swallowing step in which a subject swallows a body-insertable device with a first observing member, in an on-state, among function switches for turning on or off functions of various functional members including the first observing member and a second observing member in the body-insertable device; an observing step of observing inside of the subject in real time with an observing function of the first observing member to specify a desired site; a preparing step of preparing for an endoscopic surgical operation; a switch on step of turning on the function switch of the second observing member; and a treating step of treating the desired site with reference to an image from the first and second observing members and an image from a surgical endoscope used in the endoscopic surgical operation.

An operative treatment according to the present invention comprises a swallowing step in which a subject swallows a body-insertable device with an observing member, in an on-state, among function switches for turning on or off functions of various functional members including the observing member and a treating member in the body-insertable device; an observing step of observing inside of the subject in real time with an observing function of the observing member to specify a desired site; a switch-on step of turning on the function switch of the treating member; and a treating step of treating the desired site by the treating member with reference to an image from the observing member.

An operative treatment according to the present invention comprises a swallowing step in which a subject swallows a body-insertable device with an observing member, in an on-state, among function switches of turning on or off functions of various functional members including the observing member and a treating member in the body-insertable device; an observing step of observing inside of the subject in real time with an observing function of the observing member to specify a desired site; a preparing step of preparing for an endoscopic surgical operation; a switch-on step of turning on the function switch of the treating member; and a treating step of treating the desired site with a combination of the treating member and an endoscope treating member used in the endoscopic surgical operation, with reference to an image from the observing member and an image from a surgical endoscope used in the endoscopic surgical operation.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 67 is a flowchart showing a procedure of a sixth application example of the intra-subject medical system.

DETAILED DESCRIPTION OF THE PREFERRED EMBODIMENTS

Detailed description of the preferred embodiments of an intra-subject medical system, a method of operating body-insertable apparatus, and an operative treatment will be described.

Figure 1:
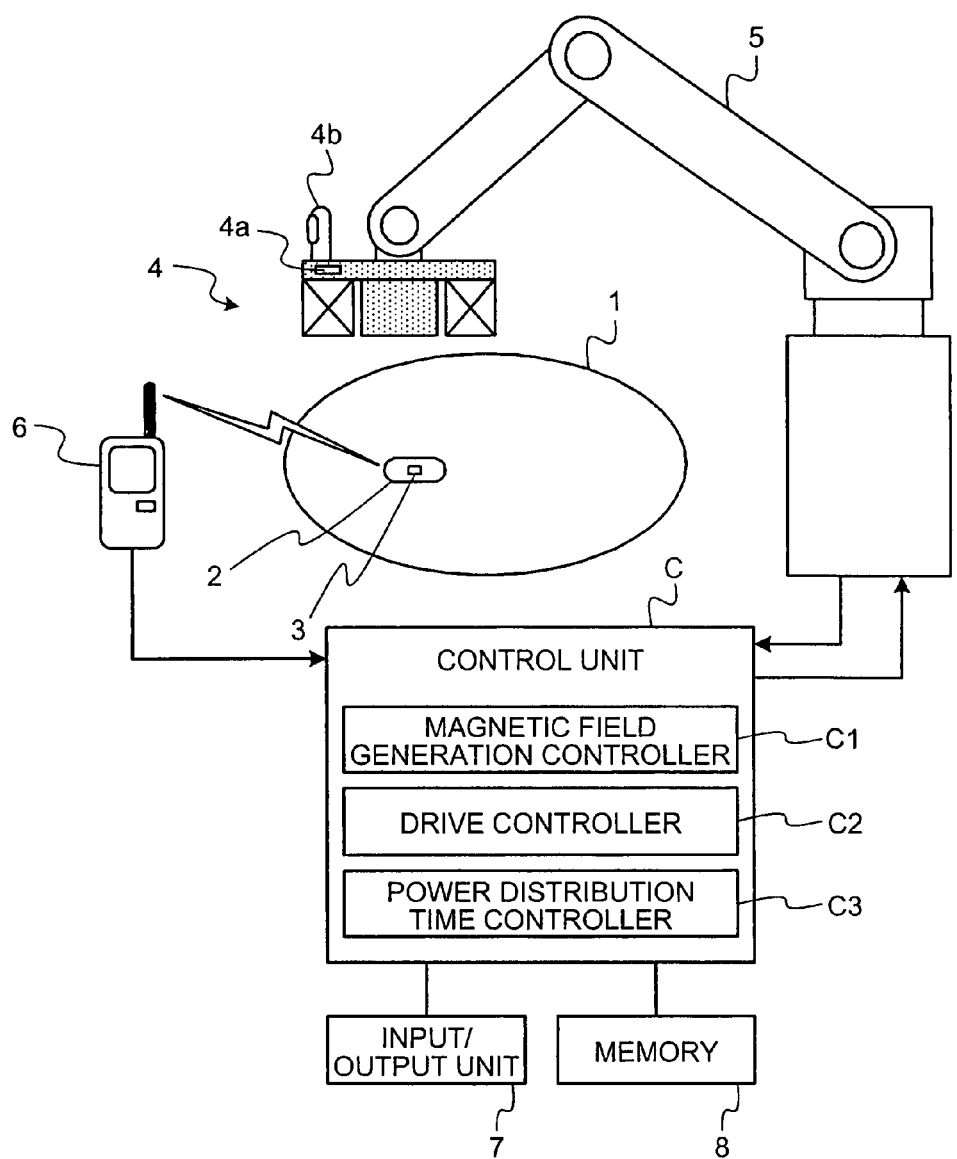
FIG. 1 is a view showing an outline structure of an intra-subject medical system according to a first embodiment of the present invention.

FIG. 1 is a view showing a general structure of an intra-subject medical system according to a first embodiment of the present invention. As shown in FIG. 1, the intra-subject medical system is introduced into a subject being tested 1 and includes a capsule endoscope 2 as a body-insertable apparatus incorporating a magnetic sensor (reed switch) 3 with directivity realized by a reed switch or the like, a magnetic field generating unit 4 composed of an electrical magnet for generating a magnetic field toward the subject 1, an arm drive unit 5 realized by a multijoint arm for moving the magnetic field generating unit 4, a viewer 6 as a receiver for receiving information sent from the capsule endoscope 2, a control unit C for controlling a magnetic field generation by the magnetic field generating unit 4 based on the information from the viewer 6 and the position of the magnetic field generating unit 4 and for controlling a magnetic field emission direction and position of the magnetic field generating unit 4 by driving the arm drive unit 5, an input/output unit 7 connected to the control unit C for inputting data to the control unit C and for outputting data from the control unit C, and a memory 8 for storing information required for the control in the control unit C.

The control unit C includes a magnetic field generation controller C1, a drive controller C2 and a power distribution time controller C3. The magnetic field generation controller C1 controls generation and stop of generation of a magnetic field emitted by the magnetic field generating unit 4. The drive controller C2 controls a drive of the arm drive unit 5. The power distribution time controller C3 detects temperature by a temperature sensor 4a disposed in the magnetic field generating unit 4 and, when the detected temperature is equal to or higher than a predetermined value, reduces the power distribution time for the magnetic field generating unit 4 to prevent an increase of temperature in the magnetic field generating unit 4. The magnetic field generating unit 4 may change its position and the emission direction by driving the arm drive unit 5 under the control of the drive controller C2; however, the magnetic field generating unit 4 may be moved by a manual operation with an operating unit 4b provided in the magnetic field generating unit 4. In this case, the amount of change at the joint portions of the arm drive unit 5 is sent to the control unit C as a movement amount.

Figure 2:
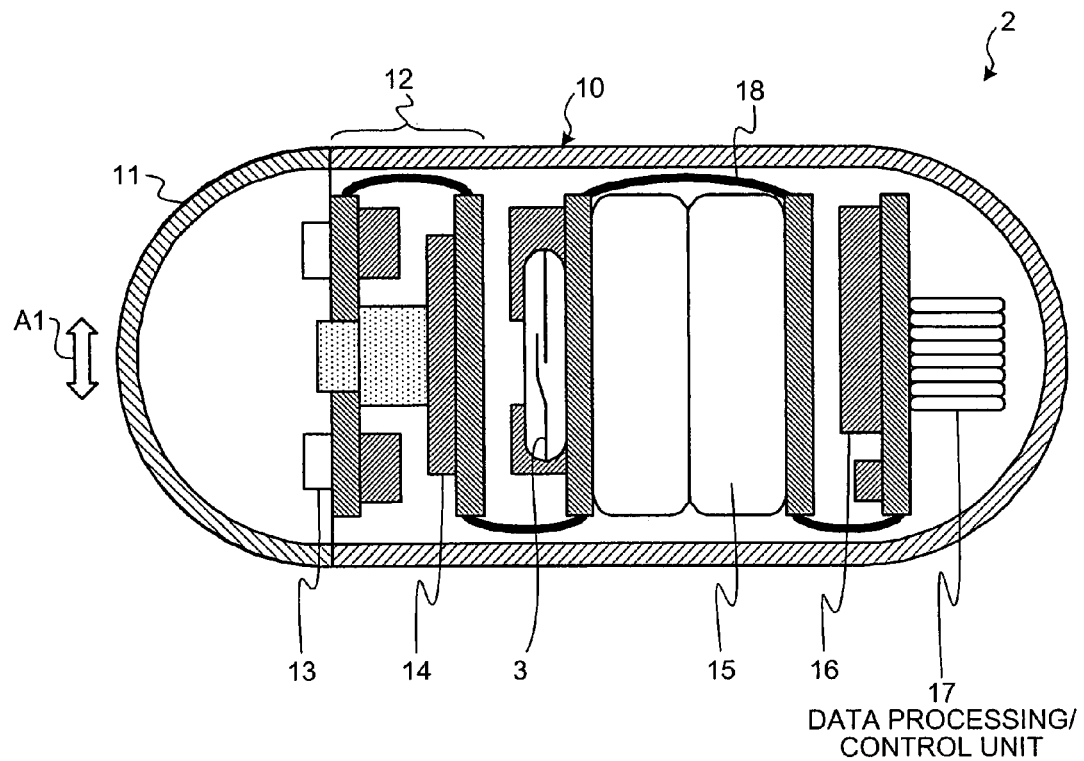
FIG. 2 is a cross-sectional view showing a structure of the capsule endoscope shown in FIG. 1.

FIG. 2 is a cross-sectional view showing a general structure of a capsule endoscope 2. As shown in FIG. 2, the capsule endoscope 2 is formed in a tubular shape having spherical ends and covered by an exterior member 10 formed in a so-called capsule shape. The exterior member 10 accommodates an observation functional unit 12, a magnetic sensor 3, a power unit 15, a data processing/control unit 16 and an antenna 17 as an observing member for emitting outside the exterior member 10 to obtain an image. Each unit is connected by a flexible wiring unit 18 and arranged in folds with respect to one another.

The observation functional unit 12 illuminates outside by an emitting unit 13 realized by an LED or the like through a transparent member 11 formed at a part of the exterior member 10, obtains an image of the illuminated region by an imaging device 14 and sends the image to the data processing/control unit 16. The obtained image is sent outside the subject via the antenna 17 as image data. The data processing/control unit 16 usually obtains two-image data in one second and sends the data outside the subject while the observation functional unit 12 is operative.

The magnetic sensor 3 has directivity for detecting magnetism. When the magnetic sensor 3 is disposed vertically with respect to the axis of the capsule endoscope, as shown in FIG. 2, the directivity directs to a direction indicated by an arrow A1. Thus, when the magnetic field strength in the direction of the arrow A1 does not exceed a strength detected by the magnetic sensor 3, the magnetic sensor 3 does not detect the magnetism of the magnetic field. When the magnetic sensor 3 detects magnetism, the data processing/control unit 16 has a function as a switch control unit for switching the current on/off states of the observation functional unit 12.

Figure 3:
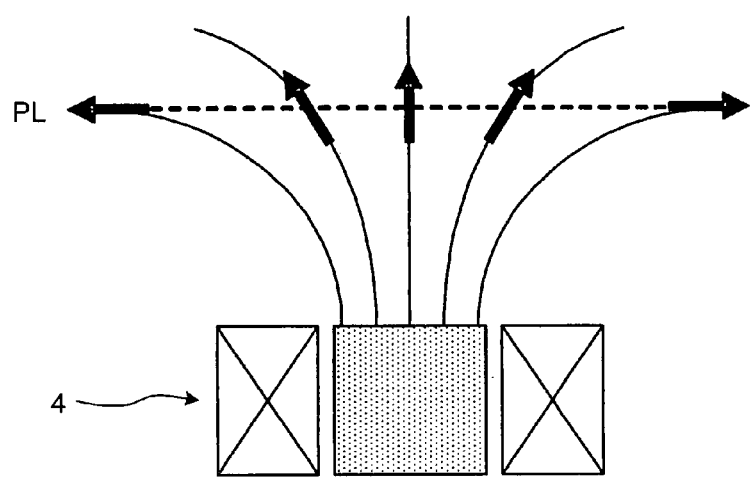
FIG. 3 is a cross-sectional view showing a magnetic force line of a magnetic field generated by a magnetic field generating unit.
Figure 4:
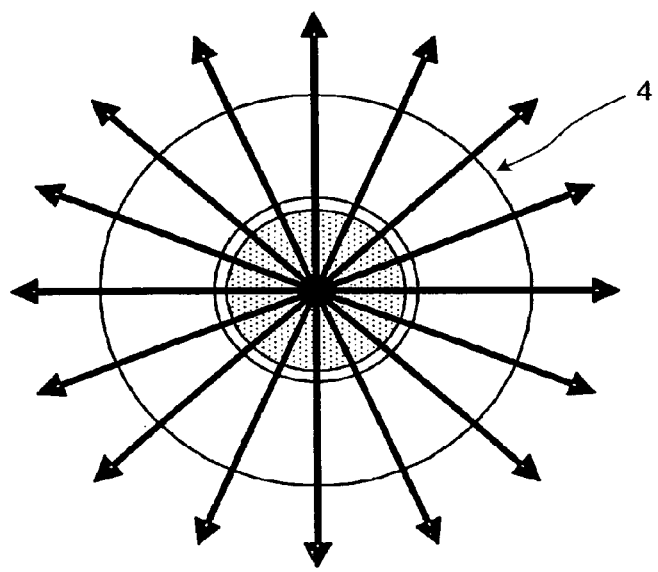
FIG. 4 is a plane view showing a magnetic force line of a magnetic field generated by the magnetic field generating unit.

On the other hand, the magnetic field generating unit 4 is an electrical magnet formed by rolling a coil around a high dielectric constant material such as an electromagnetic material. As shown in FIGS. 3 and 4, the magnetic force line of the magnetic field generating unit 4 is formed so as to spread toward the whole circumference from the center of the axis within a surface perpendicular to an axis, which is separated from the coil axis at a predetermined distance, and is gradually tilted from the axis center to circumference within a surface, which includes the axis center and is horizontal to the axis center. As a result, a magnetic force line having magnetic field directions in three dimension with respect to the inside of the subject can be easily formed.

Figure 5:
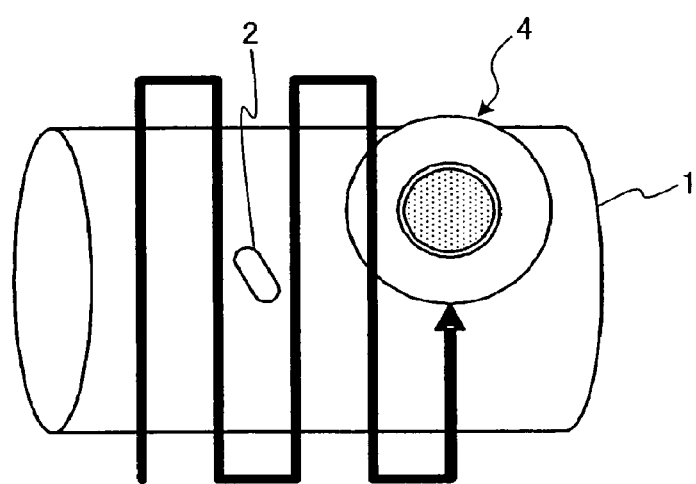
FIG. 5 is a view showing an example of a transfer pathway of the magnetic field generating unit.
Figure 6:
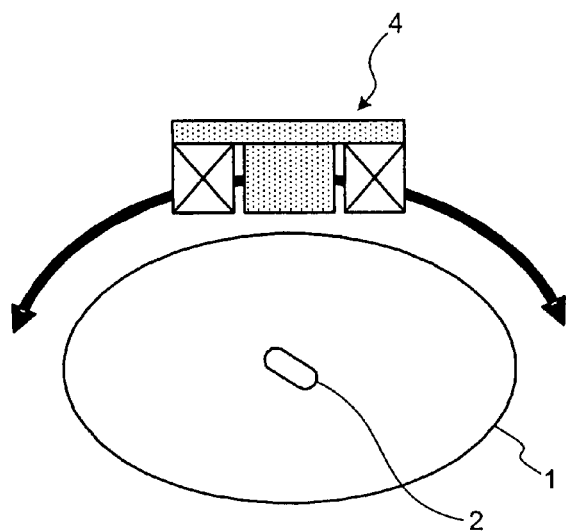
FIG. 6 is a cross-sectional view showing a transfer condition of the magnetic field generating unit.
Figure 7:
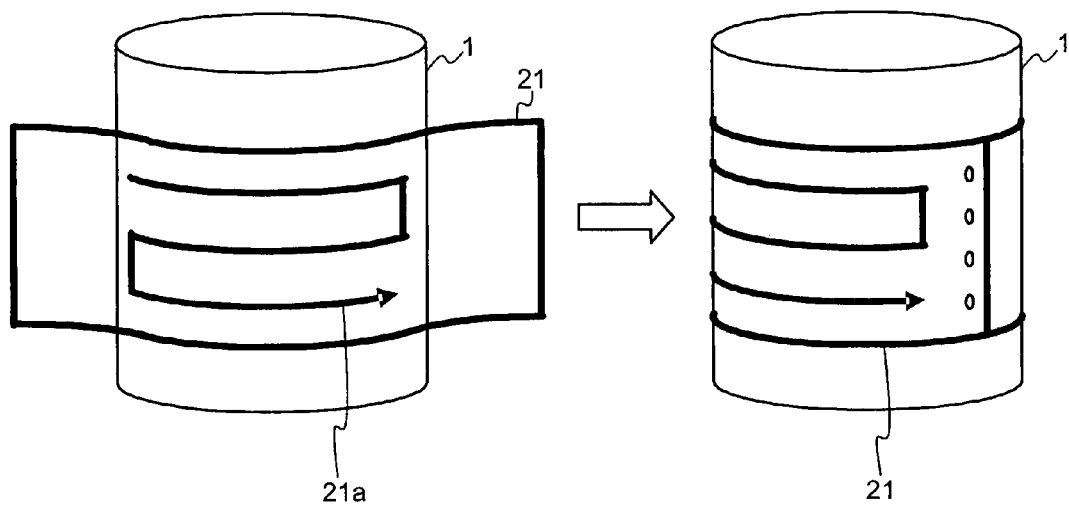
FIG. 7 is a view showing an example of a template for guiding a transfer pathway of the magnetic field generating unit.

The magnetic field generating unit 4 can be easily driven by the drive of the arm drive unit 5. As shown in FIG. 5, a magnetic force line having magnetic field directions in three dimension can be formed at every part inside the subject 1 by moving the magnetic field generating unit 4 in a zig-zag manner. Thus, magnetic field can be detected wherever the capsule endoscope 2 is located in the subject. Further, as shown in FIG. 6, when the magnetic field generating unit 4 is moved in a zig-zag manner along the surface of the subject 1, a greater magnetic field is emitted inside the subject 1 with smaller electricity consumption. When the magnetic field generating unit 4 is moved by a manual operation, as shown in FIG. 7, a template 21 indicating a transfer pathway 21a of the magnetic field generating unit 4 may be rolled around the subject 1 in advance.

Here, a process of turning on and off the observation functional unit 12 in the capsule endoscope 2 by the control unit C will be described with reference to flowcharts in FIGS. 8 and 9.

Figure 8:
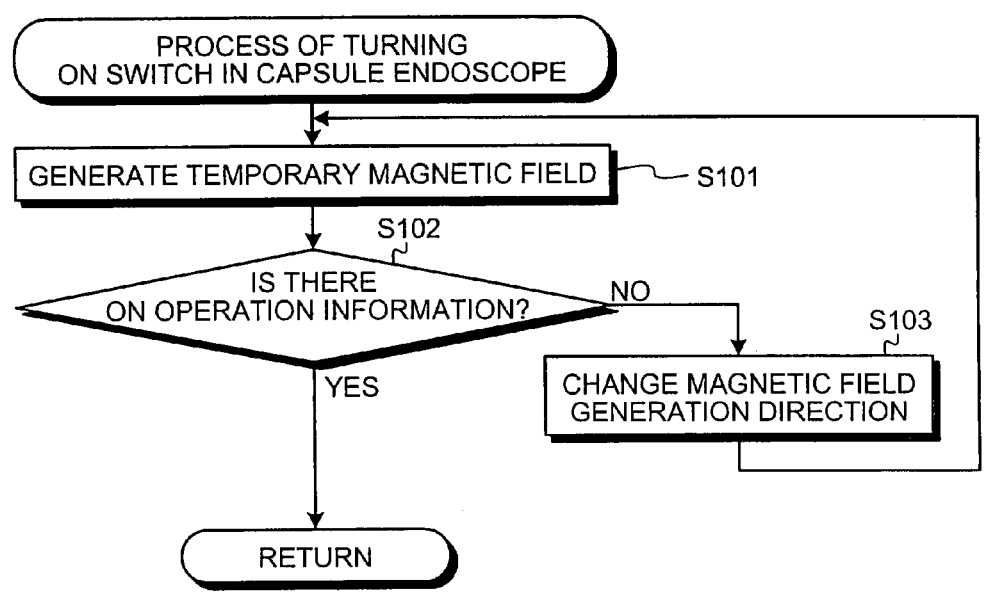
FIG. 8 is a flowchart showing a procedure for turning on a function switch in the capsule endoscope.

Firstly, a process of turning on shown in FIG. 8 is described. In this case, the observation functional unit 12 in the capsule endoscope 2 is assumed to be in an off-state. Upon receiving an instruction for turning on the observation functional unit 12, the magnetic field generation controller C1 supplies current to the magnetic field generating unit 4 to generate a temporary magnetic field toward inside of the subject 1 (step S101).

Then, the control unit C determines whether or not turn-on process information is obtained, that is, whether or not an image obtained by the observation functional unit 12 is received from the viewer 6 (step S102). When the turn-on process information is obtained (step S102, Yes), it means that the observation functional unit 12 is turned on, so the process is completed.

On the other hand, when the turn-on process information is not received (step S102, No), the drive controller C2 moves the magnetic field generating unit 4 in order to change the direction of generated magnetic field (step S103), and then, the procedure goes back to step S101. The above procedure is repeated until the turning on process information is received.

Figure 9:
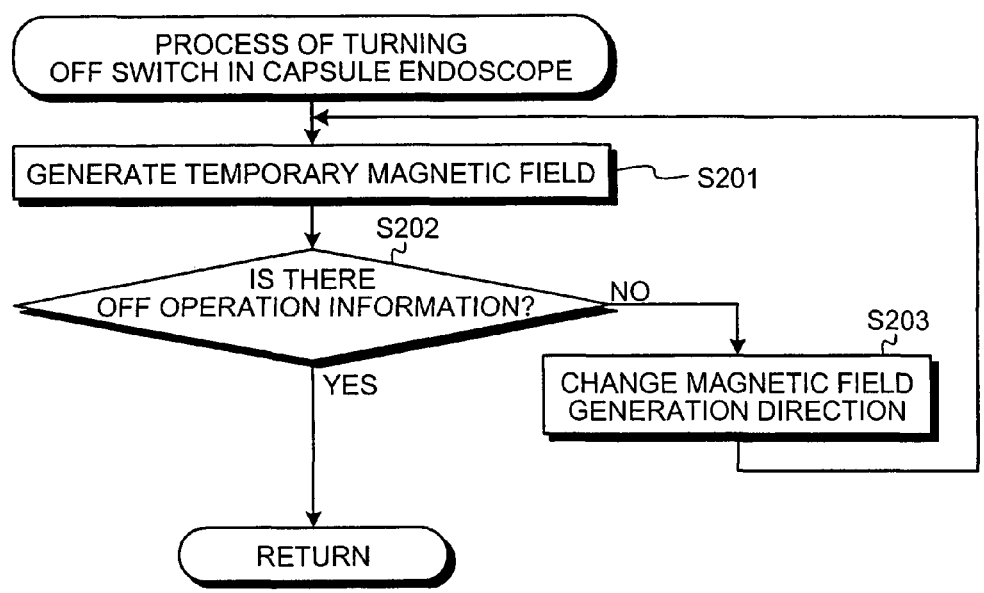
FIG. 9 is a flowchart showing a procedure for turning off the function switch in the capsule endoscope.

Next, a process of turning off, shown in FIG. 9, is described. In this case, the observation functional unit 12 in the capsule endoscope 2 is assumed to be in an on-state. Upon receiving an instruction for turning off the observation functional unit 12, the magnetic field generation controller C1 supplies current to the magnetic field generating unit 4 to generate a temporary magnetic field inside the subject 1 (step S201).

Then, the control unit C determines whether or not turn-off process information is obtained, that is, whether or not the image obtained by the observation functional unit 12 is no more received from the viewer 6 (step S202). When the turning off process information is obtained (step S202, Yes), it means that the observation functional unit 12 is turned off, so the procedure is completed.

On the other hand, when the turning off process information is not obtained (step S202, No), the drive controller C2 moves the magnetic field generating unit 4 in order to change the direction of the magnetic field (step S203), and then, the procedure goes back to step S201. The above process is repeated until the turning off process information is obtained.

Here, generation of the temporary magnetic field from the magnetic field generating unit 4 by the magnetic field generation controller C1 will be described. The magnetic sensor 3 in the capsule endoscope 2 is a magnetism switch which is turned on when a magnetism equal to or greater than a predetermined value is detected and is turned off when a magnetism smaller than a predetermined value is detected. Thus, the magnetic field generating unit C1 generates a magnetic field with magnetism equal to or greater than the predetermined value toward the magnetic field generating unit 4 for a predetermined period of time or longer. When the magnetic sensor 3 is turned on for the predetermined period of time or longer, the data processing/control unit 16 controls to turn on the observation functional unit 12, even when the magnetic sensor 3 is turned off. The control of the data processing/control unit 16 for turning on the observation functional unit 12 is implemented when the observation functional unit 12 is in an off-state before the control is implemented. Therefore, when the observation functional unit 12 before controlled is in an on-state, the observation functional unit 12 is turned off by the same control. That is, the on/off states of the magnetic sensor 3 and the on/off states of the observation functional unit 12 is not associated and, when the magnetic sensor 3 is in an off-state for the predetermined period of time or longer, the data processing/control unit 16 controls the on/off states of the observation functional unit 12 in a toggle operation. With this structure, electricity consumption for generating magnetic field can be reduced and the on/off states of the observation functional unit 12 can be securely maintained.

Figure 10:
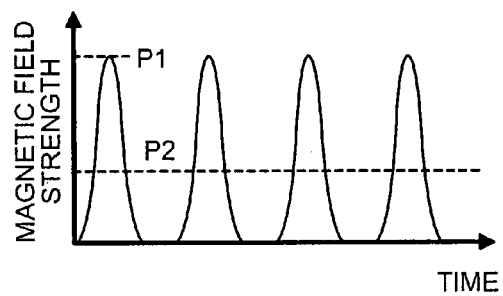
FIG. 10 is a view showing an example of a pulse generated by the magnetic field generating unit.

As shown in FIG. 10, a magnetic field may be generated in a pulsed condition. Upon detecting a magnetic field strength (magnetism strength) equal to or greater than the predetermined value, the magnetic sensor 3 is turned on. Accordingly, when a magnetic field is generated in a pulsed condition, the state of the magnetic sensor 3 is switched with smaller electricity consumption, compared to a case of generating a DC magnetic field. In particular, since the magnetism is attenuated inversely proportional to the cube of the distance, it is very effective that the magnetic field is generated in a pulsed condition. However, since the magnetic field is pulsed condition, the magnetic sensor 3 is repeatedly turned on and off at every beginning and end of the pulsed magnetic field. Accordingly, the data processing/control unit 16 controls the toggle operation of the observation functional unit 12 more than once in a predetermined period of time when the magnetic sensor is turned on. Here, the pulse frequency is set to be equal to or less than a resonance frequency of a processing circuit (not shown) for processing outputs of a detector of the magnetic sensor 3 and the magnetic sensor 3 so that the magnetic sensor 3 is surely operated.

Figure 11:
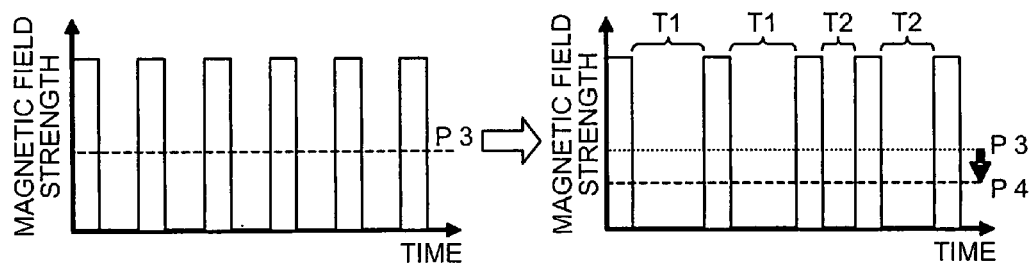
FIG. 11 is a view showing an example of a pulse in which a pulse interval is varied according to movement speed of the magnetic field generating unit.

Further, regarding the magnetic field in a pulsed condition, when the magnetism pulse is controlled to be generated not at constant intervals but at intervals corresponding to a movement speed of the magnetic field generating unit 4 as shown in FIG. 11, electricity consumption can be further reduced. In other words, when the movement speed of magnetic field generating unit 4 is fast, the intervals of pulse generation are made smaller and, when the movement speed of magnetic field generating unit 4 is slow, the intervals of pulse generation are made larger. For example, simply, when the magnetic field generating unit 4 is not moved, magnetism pulse may be generated at intervals T1 and, when the magnetic field generating unit 4 starts to be moved, magnetism pulse may be generated at intervals T2. With this structure, variations of magnetic field density on the surface of the subject 1 are prevented, and also, electricity consumption can be reduced.

Figure 12:
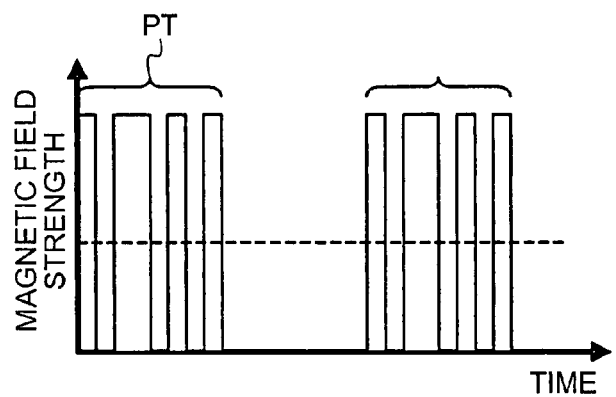
FIG. 12 is a view showing an example of a pulse pattern including a switch on/off control information.

Here, as shown in FIG. 12, magnetism may be generated according to a predetermined pattern PT. The magnetic sensor 3 is turned on or off in response to the pattern PT. The data processing/control unit 16 determines whether or not it is the predetermined pattern PT based on the on/off states of the magnetic sensor 3 and, when it is determined as the predetermined patter, the observation functional unit 12 is controlled to be in an on-state or off-state. In this case, different patterns are prepared for turning on the observation functional unit 12 and for turning off the observation functional unit 12. The observation functional unit 12 can be controlled to be in a desired state regardless of its current state. Further, in a case in which functional units other than the observation functional unit 12 are included, different patterns may be prepared corresponding to each functional unit so that the on/off states of the functional units can be controlled by the single magnetic sensor 3.

Figure 13:
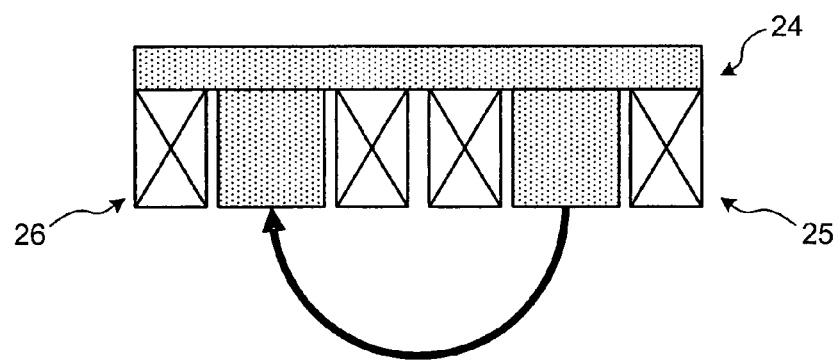
FIG. 13 is a cross-sectional view showing a magnetic field generating unit, in which two electrical magnets are arranged parallel to each other.

Further, the above-described magnetic field generating unit 4 includes a single electrical magnet; however, as shown in FIG. 13, two electrical magnets may be provided. A magnetic field generating unit 24 in FIG. 13 includes two electrical magnets 25, 26 which are arranged parallel to each other so that those polar characters are arranged opposite to each other. A loop of the magnetic force line is formed by the electrical magnets 25, 26 and a strong magnetic field can easily be formed in a direction perpendicular to the axes of the electrical magnets 25, 26.

Figure 14:
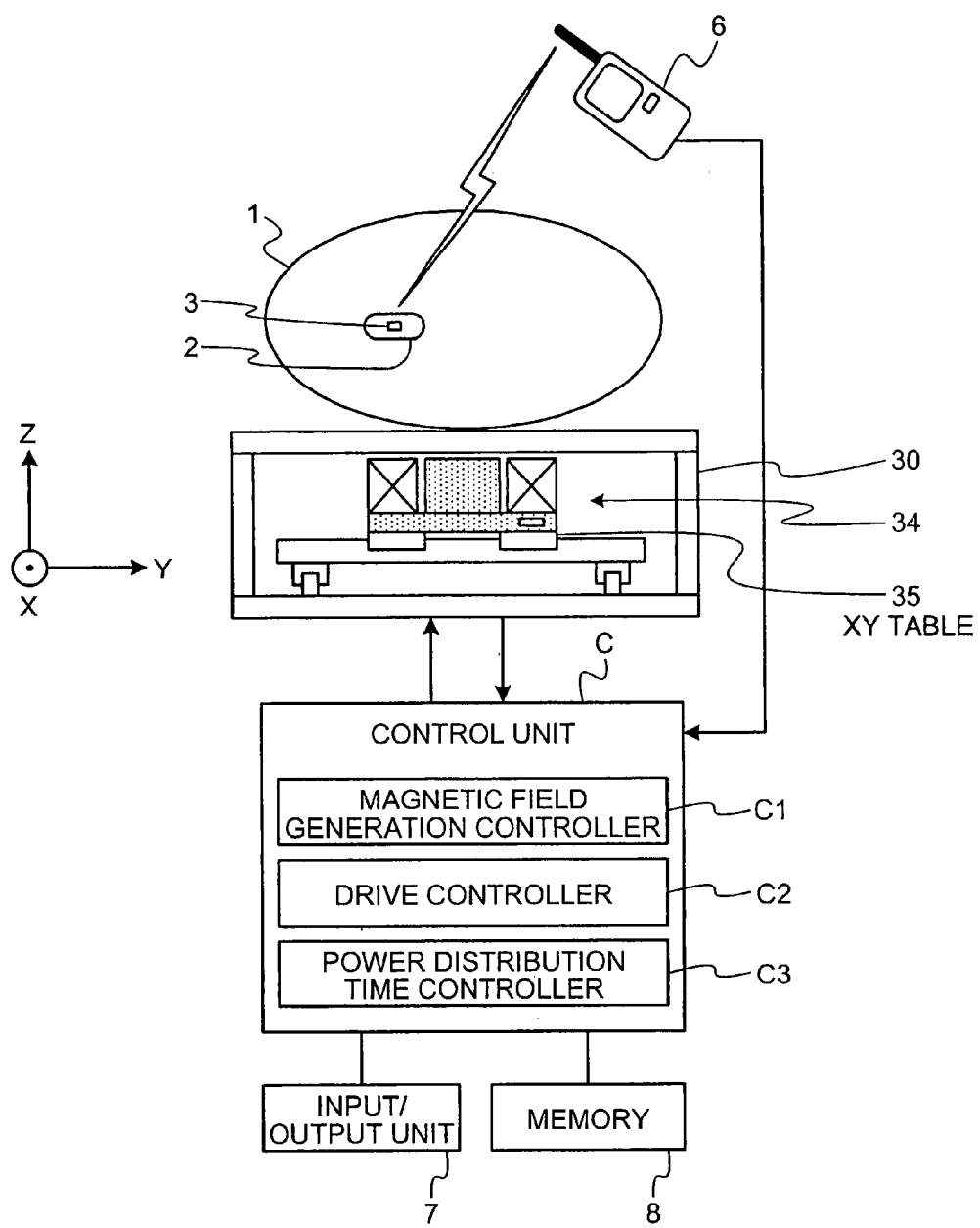
FIG. 14 is a view showing a general structure of an intra-subject medical system, in which a movement of the magnetic field generating unit is realized by an XY table.

Furthermore, the above-described magnetic field generating unit 4 is moved by the arm drive unit 5 of a multijoint arm; however, as shown in FIG. 14, an XY table 35 may be provided in the mounting base 30 on which the subject 1 lies. Here, on the XY table 35, a magnetic field generating unit 34 having the same structure as that of the magnetic field generating unit 4 may be provided, and under the control of the drive controller C2, the magnetic field generating unit 34 may be configured to be moved in two dimensional directions. According to the intra-subject medical system shown in FIG. 14, the space in the mounting base 30 is used effectively so that a system requiring a smaller space can be realized.

Figure 15:
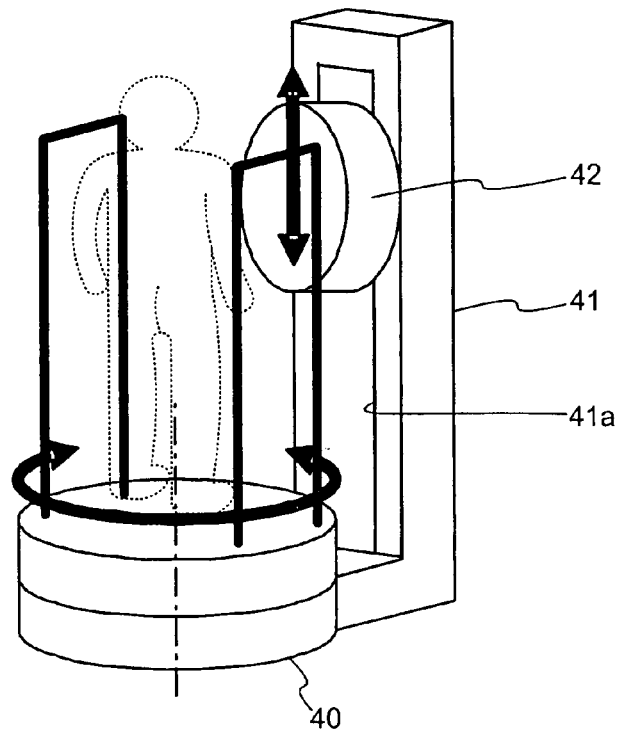
FIG. 15 is a schematic view showing another example of a system for moving the magnetic field generating unit.

Further, the on/off states of the observation functional unit 12 in the capsule endoscope 2 may be controlled while the subject 1 is standing up. As shown in FIG. 15, the system includes a rotary base 40 and a support unit 41 for supporting the magnetic field generating unit 42. The magnetic field generating unit 42 moves on a vertically extending guide 41*a* of the support unit 41 to generate a magnetic field toward the subject 1. With the combination of the up-and-down movement of the magnetic field generating unit 42 and the rotation of the rotary base 40, the emission direction of the magnetic field can be varied.

Figure 16:
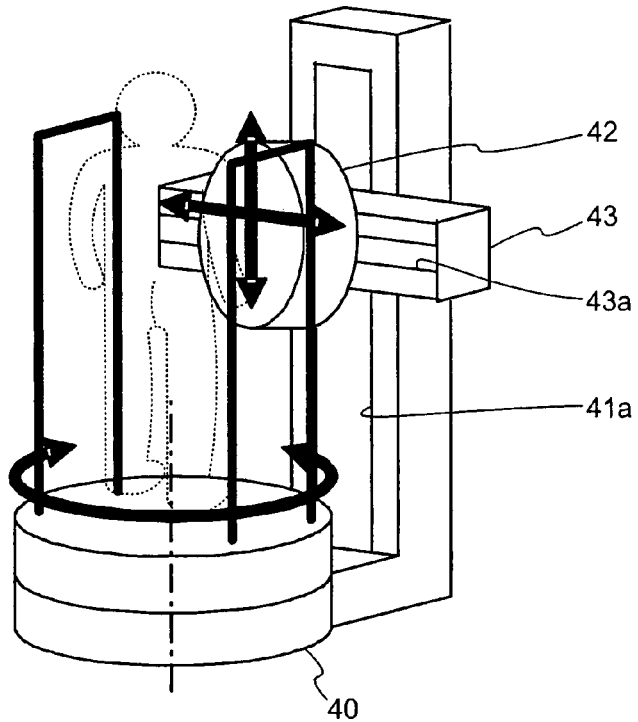
FIG. 16 is a schematic view showing another example of a system for moving the magnetic field generating unit.

The system shown in FIG. 16 is a system for emitting a magnetic field to the subject 1 standing up. According to this system, a support unit 43 which moves up and down on the guide 41*a* of the support unit 41 is further provided so that the magnetic field generating unit 42 moves horizontally on the horizontally-provided guide 43*a* of the support unit 43. Accordingly, the magnetic field generating unit 42 can be movable in the up-and-down (vertical) direction and the horizontal direction. In this case, a wiggle movement of the rotary base 40 is prevented and the motionless condition of the subject 1 can be maintained more easily so that the switching of the state the observation functional unit 12 can be securely implemented.

Figure 17:
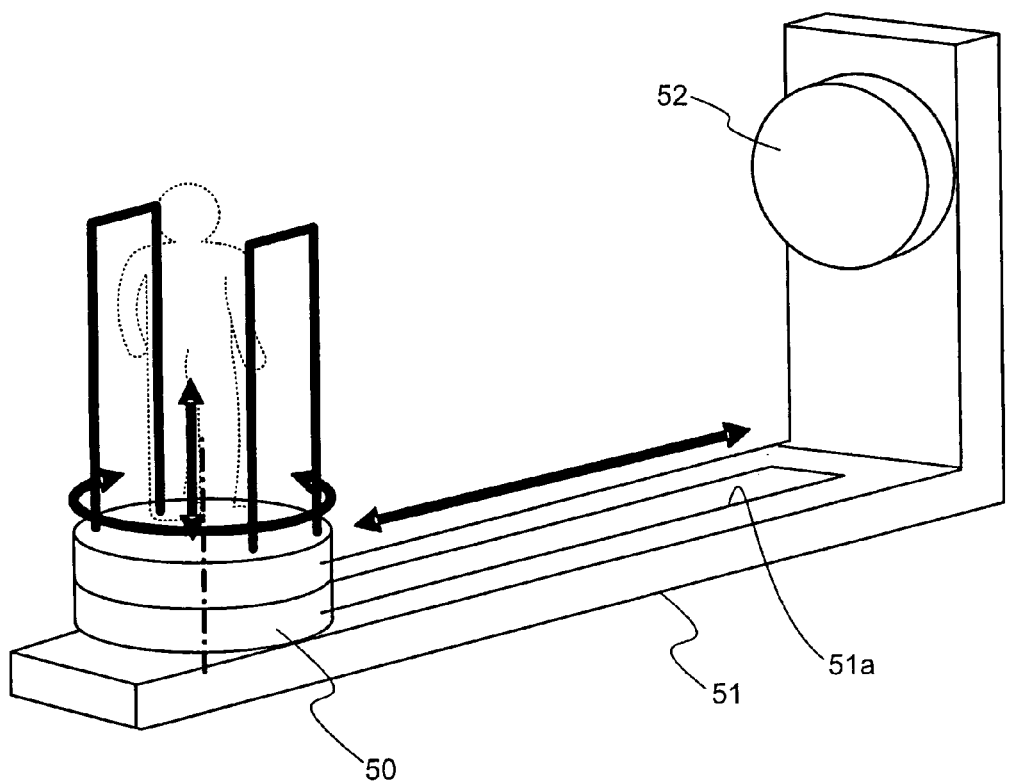
FIG. 17 is a schematic view showing an example of a system for relatively moving the magnetic field generating unit.

According to the above-described system, the subject 1 is assumed to be motionless and the magnetic field generating units 4, 42 are moved; however, the subject 1 may be moved to switch the state of the observation functional unit 12 in the capsule endoscope 2 introduced into the subject 1 while the magnetic field generating unit is kept motionless. For example, as shown in FIG. 17, a rotary base 50 for rotating the subject 1 who is standing up and a support unit 51 for fixing a magnetic field generating unit 52 and movably supporting the rotary base 50 may be included and the rotary base 50 may be moved on a guide 51*a* provided on the support unit 51 to put the subject 1 close to the magnetic field generating unit 52.

Figure 18:
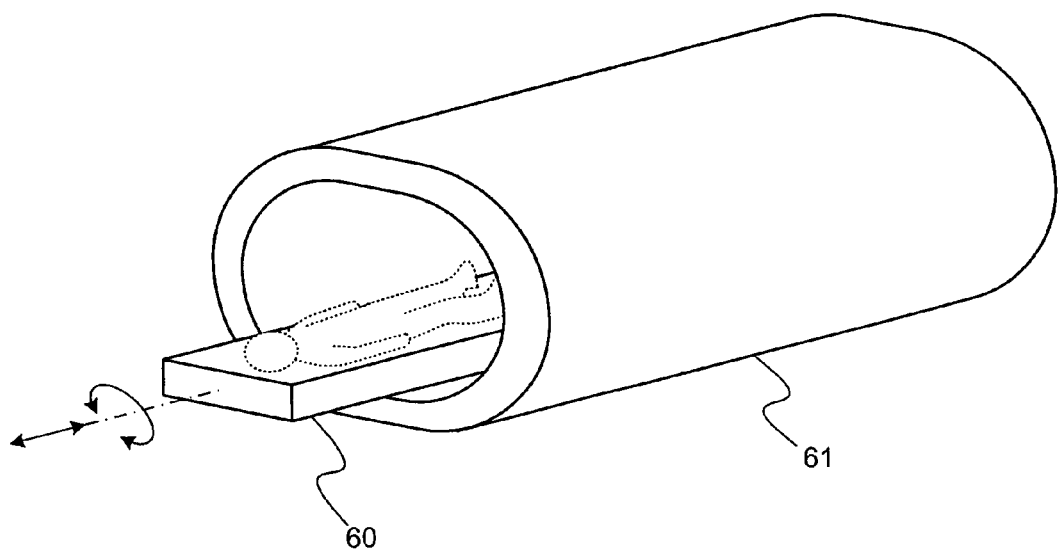
FIG. 18 is a schematic view showing an example of a system for relatively moving the magnetic field generating unit.

Further, as shown in FIG. 18, the system may include a tubular shaped magnetic field generator 61 and a mounting base 60 for mounting the subject 1 and a magnetic field may be emitted to the subject 1 by inserting/removing the mounting base 60 into/from the magnetic field generator 61. In this case, the mounting base 60 is preferably rotatable about the axis of inserting and removing direction.

The magnetic field generating units 4, 34, 42, 52 and the magnetic field generator 61 are realized by an electrical magnet or a magnet coil; however, the present invention is not limited to this and a permanent magnet may be employed to generate a magnetic field. However, when a permanent magnet is employed, since the permanent magnet constantly generates a magnetic field, a measure for the case the magnetic field is not used is needed.

Figure 19:
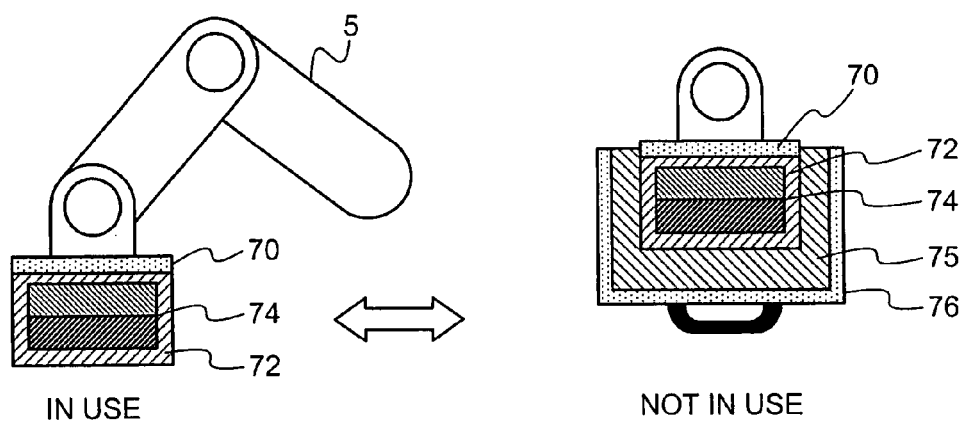
FIG. 19 is a view showing an example in which the magnetic field generating unit is composed of a permanent magnet.

For example, as shown in FIG. 19, the circumference of the permanent magnet 74 is covered by a nonmagnetic resin 72 and connected to the arm drive unit 5 via a base unit 70 made of a ferromagnetic material. With this structure, a magnetic field generating unit using a permanent magnet 74 can be realized. When the magnetic field is not used, the magnetic field generating unit is covered by a casing unit 76 made of a ferromagnetic material from an end of the magnetic field generating unit to cover the permanent magnet 74 with the base unit 70 and the casing unit 76 made of an electromagnetic material so as to reduce leakage of the magnetic field. In FIG. 19, a spacer 75 is disposed inside the casing unit 76.

Figure 20:
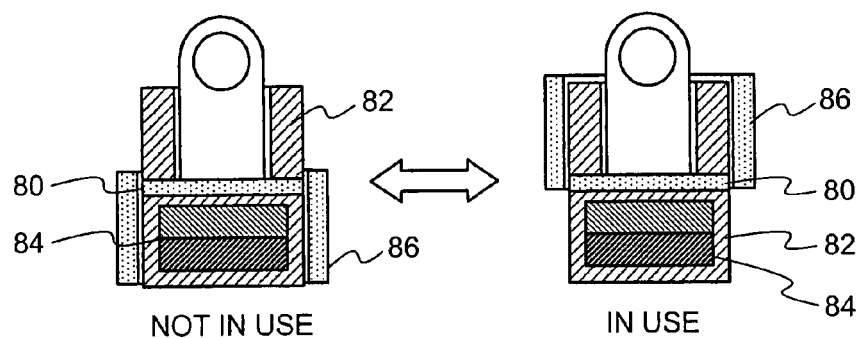
FIG. 20 is a view showing an example in which the magnetic field generating unit is composed of a permanent magnet.

Further, as shown in FIG. 20, a casing unit 86 corresponding to the casing unit 76 may be provided to the arm drive unit 5 in advance. In this case, a resin 82 includes a guide for guiding the casing unit 86 so that the casing unit 86 moves on the guide to block the magnetic field when the magnetic field is not used. The casing unit 86, shown in FIG. 20, is not required to cover the whole circumference of the permanent magnet 84 and may be provided so as to block the magnetic force line of the permanent magnet 84.

Figure 21:
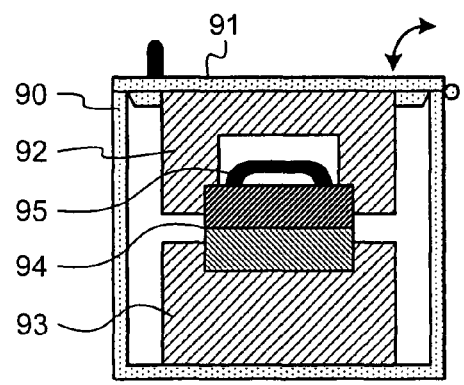
FIG. 21 is a cross-sectional view showing a condition of stored magnetic field generating unit composed of the permanent magnet.
Figure 22:
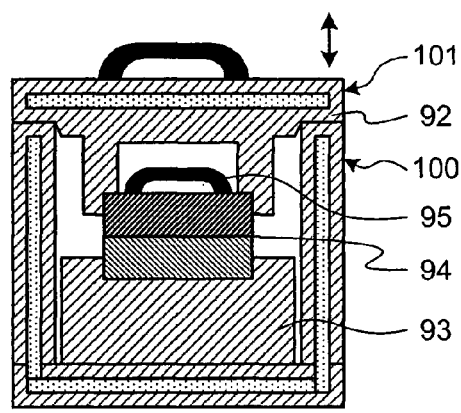
FIG. 22 is a cross-sectional view showing a condition of stored magnetic field generating unit composed of the permanent magnet.

Furthermore, as shown in FIG. 21, a permanent magnet 94 may be removably attached to an end of the arm drive unit 5 and stored in a box 90 made of a ferromagnetic material when the magnetic field is not required. In FIG. 21, a support unit 93 made of a nonmagnetic resin is provided in the bottom of the box 90, which has an opening in its upper portion and is made of a ferromagnetic material. The permanent magnet 94 is disposed on the support unit 93 and the opening of the box 90 is covered by a cover unit 91, which is made of a ferromagnetic material and has a support unit 92 made of a nonmagnetic resin on its bottom surface. The permanent magnet 94 includes a gripper 95 for moving the permanent magnet 94. Further, the permanent magnet 94 is not required to be disposed at an end of the arm drive unit 5 and may be held by an operator to be put closer to the subject 1 to generate a magnetic field inside the subject. As shown FIG. 22, a cover unit 101 and a box unit 100 may be separatably provided.

Figure 23:
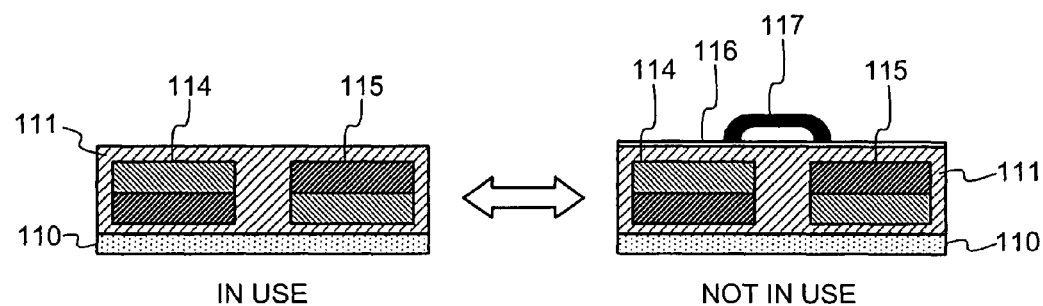
FIG. 23 is a cross-sectional view showing the magnetic field generating unit composed of two electrical magnets, which are arranged parallel to each other.

Further, when a magnetic field generating unit is provided with a permanent magnet, as shown in FIG. 23, two permanent magnets may be arranged in parallel in order to generate a strong magnetic field. For example, as shown in FIG. 23, two permanent magnets 114, 115 are arranged parallel to each other so that those polar characters are arranged opposite to each other at a face of a support unit 110 made of a ferromagnetic material and each circumference of the permanent magnets 114, 115 is covered by a nonmagnetic resin 111. In this magnetic field generating unit, also, a cover unit 116, which is made of a ferromagnetic material and has a gripper 117 is provided on the other side of the support unit 110 so as to sandwich the permanent magnets 114, 115 in order to reduce leak of the magnet field when the magnet field is not used. In this case, a magnetism circuit, in which the magnetic force line forms a closed loop, is generated by the permanent magnets 114, 115, the cover unit 116 and the support unit 110 and leakage of the magnetic field can be prevented.

Figure 24:
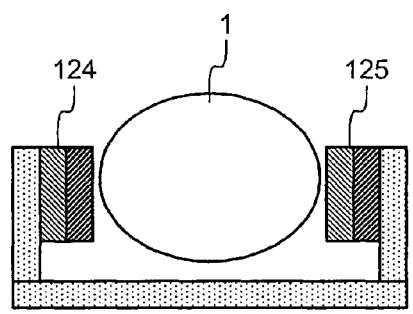
FIG. 24 is a cross-sectional view showing the magnetic field generating unit composed of two electrical magnets, which are arranged facing each other.
Figure 25:
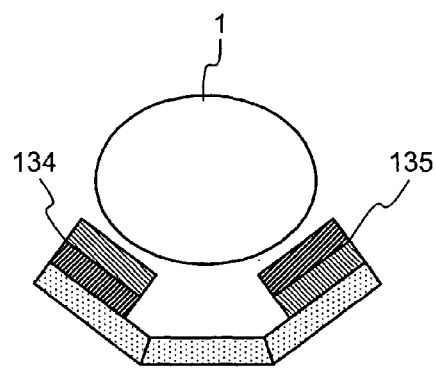
FIG. 25 is a cross-sectional view showing the magnetic field generating unit composed of two electrical magnets, which are slightly displaced from the positions where they face each other.

Further, when the magnetic field generating unit is realized by a permanent magnet, as shown in FIG. 24, the permanent magnets 124, 125 may be arranged opposite while sandwiching the subject 1. In this case, when a member for supporting the permanent magnets 124, 125 is made of a ferromagnetic material, a magnetism circuit is formed and leakage of the magnetic field can be prevented. As shown in FIG. 25, the permanent magnets 134, 135 may be displaced from the positions where they face each other. This oblique arrangement may provide a blank space around the size of the subject 1. In each of the cases, the subject 1 is placed on the magnetism circuit.

Figure 26:
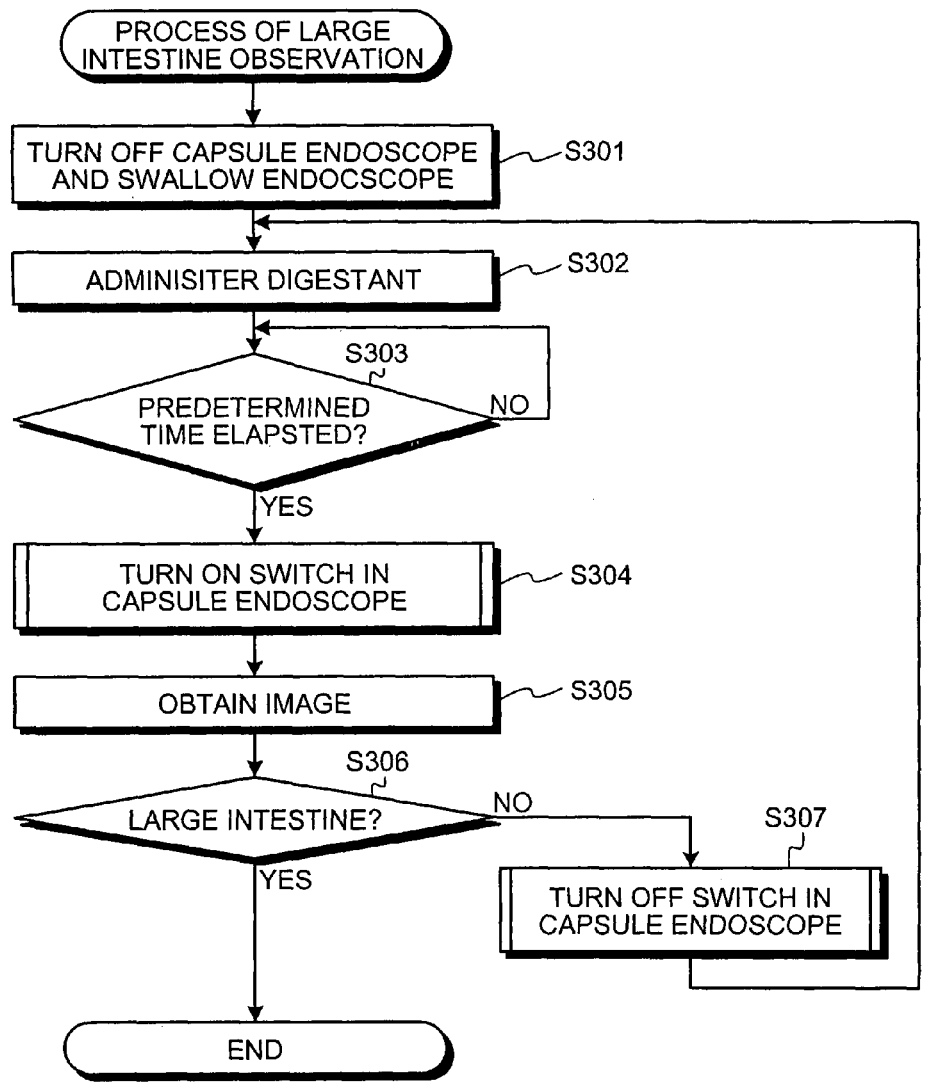
FIG. 26 is a flowchart showing a procedure for operating the capsule endoscope when the intra-subject medical system is used for a large intestine observation.

A method of using the intra-subject medical system will be described. Firstly, a method of using the system to observe the large intestine will be explained with reference to FIG. 26. As shown in FIG. 26, the functional units including the observation functional unit 12 of the capsule endoscope 2 are turned off and swallowed by a person to be examined (step S301). Then, a digestant for promoting digestion is administered to accelerate the movement of the capsule endoscope 2 (step S302). Then, it is determined whether or not a predetermined period of time has elapsed (step S303), and, only when the predetermined period of time has elapsed (step S303, Yes), a process of turning on is implemented to turn on the function switch in the capsule endoscope 2 (step S304, See FIG. 8). An image sent by the capsule endoscope 2 is received (step S305) and it is determined whether or not the image is an image showing the large intestine (step S306). When the large intestine is not shown in the image (step S306, No), an process of turning off is implemented to turn off the function switch in the capsule endoscope 2 (step S307, See FIG. 9), and then, the procedure goes back to step S302 to repeat the above procedure. On the other hand, when the large intestine is shown in the image (step S306, Yes), the procedure ends. In this condition, the capsule endoscope 2 in the large intestine moves corresponding to peristaltic movements of the large intestine and sequentially takes images in the large intestine to send the images outside the subject 1. In this way, the large intestine can be observed.

Figure 27:
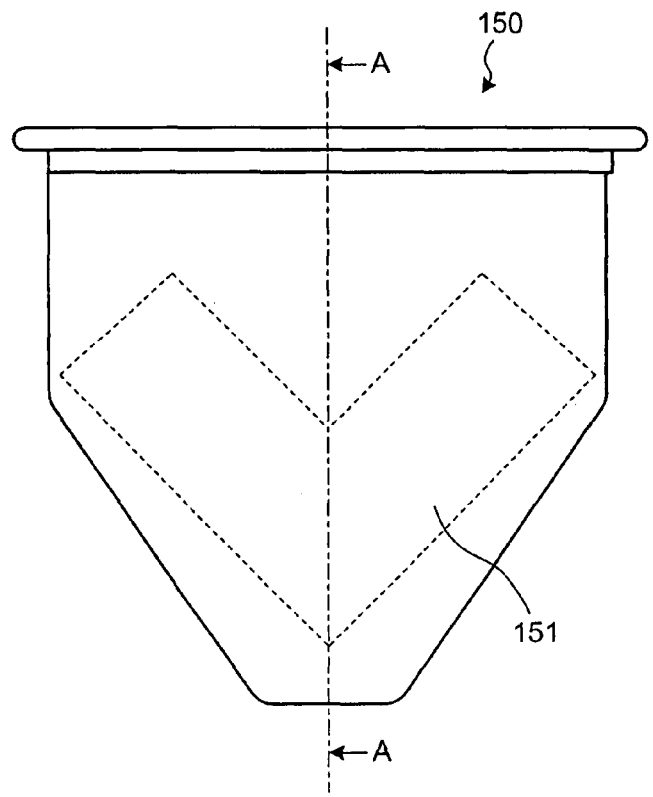
FIG. 27 is a diagrammatic front view showing a structure example of the magnetic field generating unit.
Figure 28:
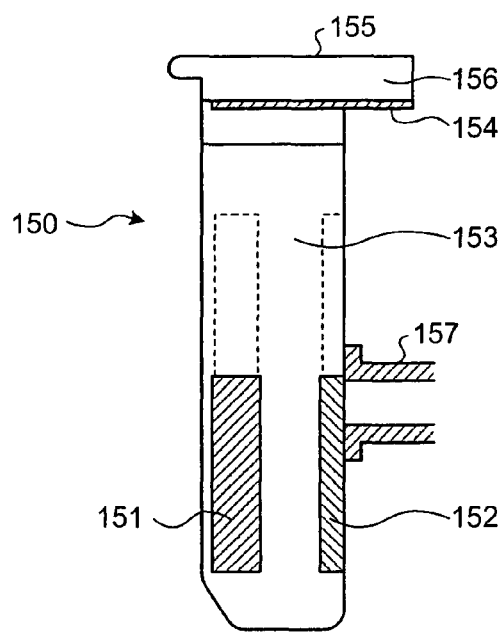
FIG. 28 is a cross-sectional view taken along a line A-A in FIG. 27.
Figure 29:
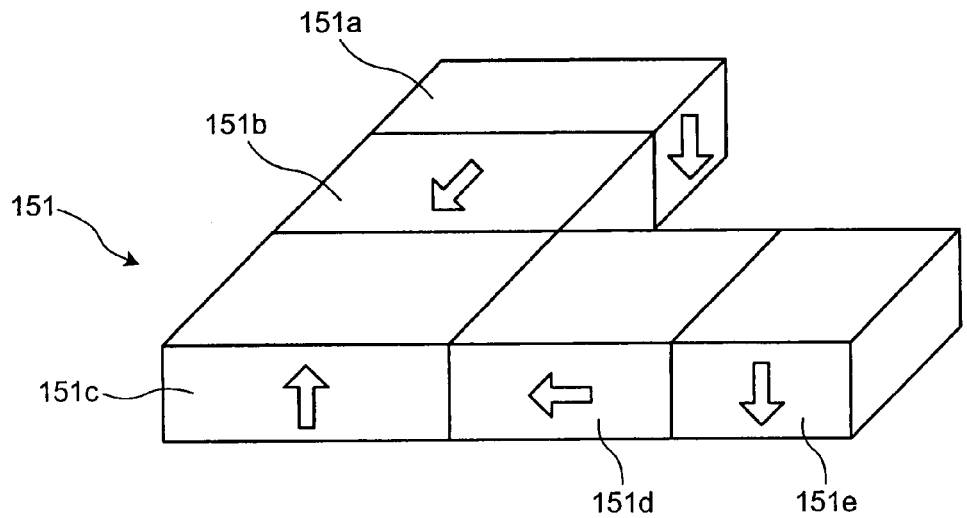
FIG. 29 is a diagrammatic perspective view showing a structure example of the permanent magnet.
Figure 30:
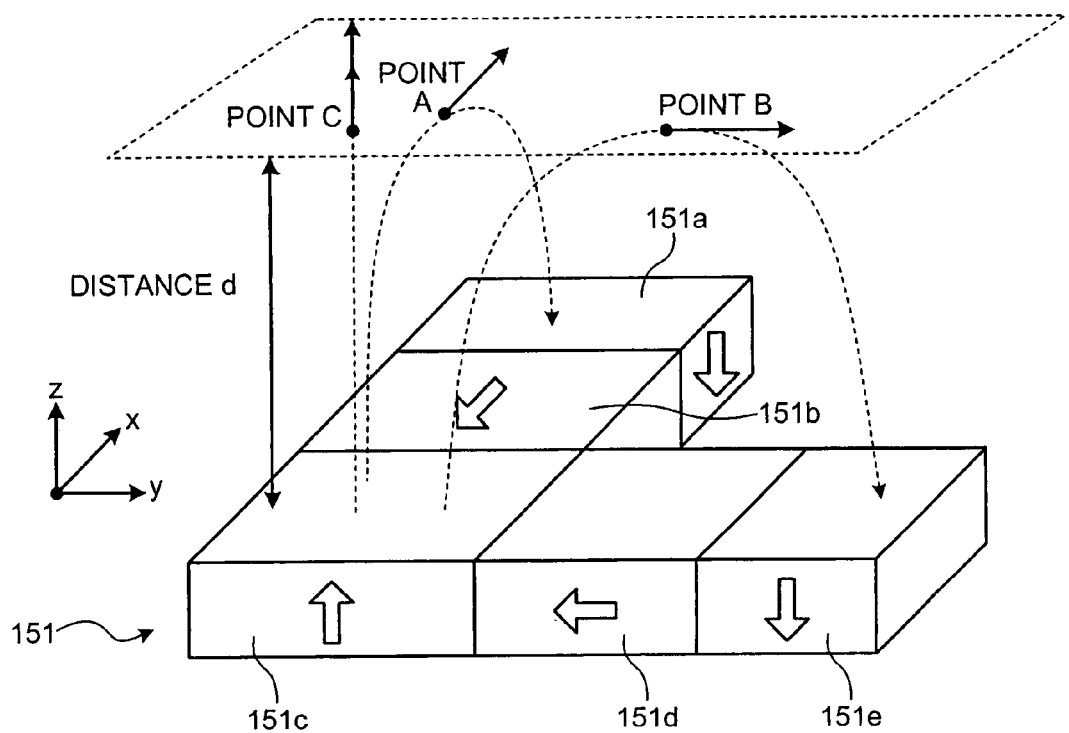
FIG. 30 is a diagrammatic perspective view showing a direction of magnetic field generated by the permanent magnet.

Here, a magnetic field generator composed of a magnetic field generating unit, a magnet housing unit, an elevating unit and the like will be described as a more detailed example of a magnetic field generator using a permanent magnet. FIG. 27 is a diagrammatic front view showing a structure example of the magnetic field generating unit and FIG. 28 is a cross-sectional view taken along a line A-A in FIG. 27. A magnetic field generating unit 150 has its lower portion in a taper shape so as to be easily stored in a magnet housing unit and includes a permanent magnet 151 therein. The permanent magnet 151 is, as shown in FIG. 29, composed of five blocks 151*a* to 151*e* which are integrally combined in a V shape. Thick arrows in FIG. 29 indicate magnetization directions of each block 151*a* to 151e. FIG. 30 shows a direction of magnetic field generated by the permanent magnet 151 composed as described above. Dashed lines indicate directions of a main magnetic field and thin arrows indicate directions of magnetic field on a plane surface. According to the example shown in FIG. 30, a magnetic field at a position A is generated in a direction x, a magnetic field at a position B is generated in direction y and a magnetic field at a position C is generated in a direction z.

With such a magnetic field generating unit 150, a magnetic field required for switching operation can be generated in all directions x, y and z at a position on a plane surface, which is separated from a front surface of the magnetic field generating unit 150 by a predetermined distance d. Further, as shown in FIG. 29, magnetization directions of each block 151a to 151e are set so that magnetic field generated toward back side (the direction of −z) can be reduced. Further, as shown in FIG. 28, the magnetic field generating unit 150 includes a magnetic material 152 formed in a same V shape as the permanent magnet 151 behind the permanent magnet 151 via a nonmagnetic material 153 so as to further suppress the magnetic field leakage behind the permanent magnet 151. The nonmagnetic material 153 covers the whole circumference of the permanent magnet 151. As shown in FIGS. 27 and 28, above the magnetic field generating unit 150, a cover 156 composed of the magnetic material 154 and the nonmagnetic material 155 is provided. Behind the magnetic field generating unit 150, a connection arm 157 is connected.

Figure 31:
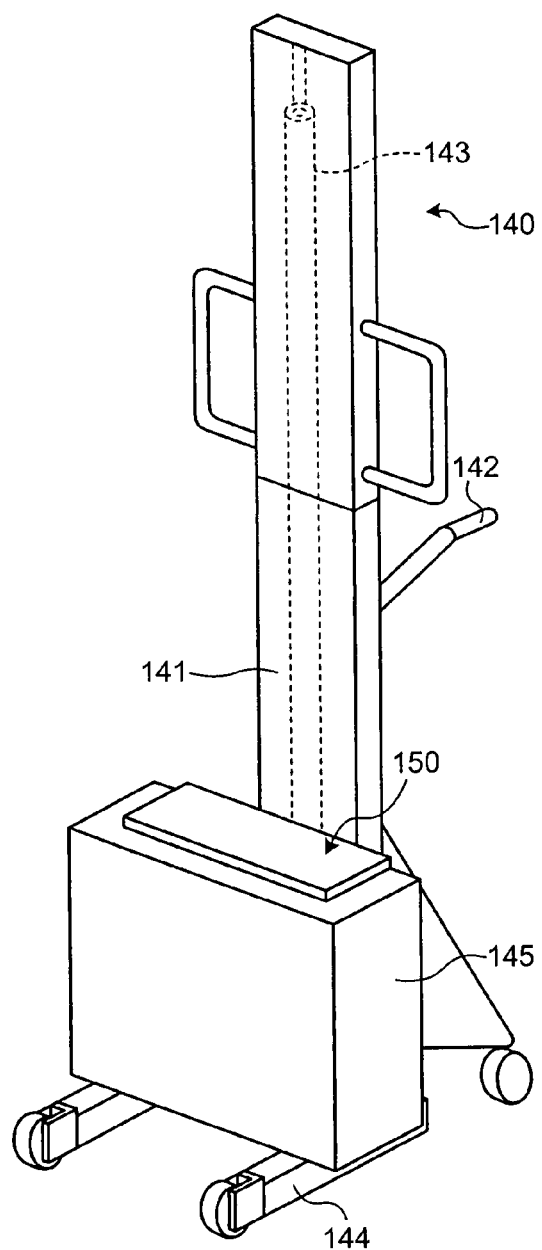
FIG. 31 is a diagrammatic perspective view showing an entire structure of a magnetic field generator 140 when not used.
Figure 32:
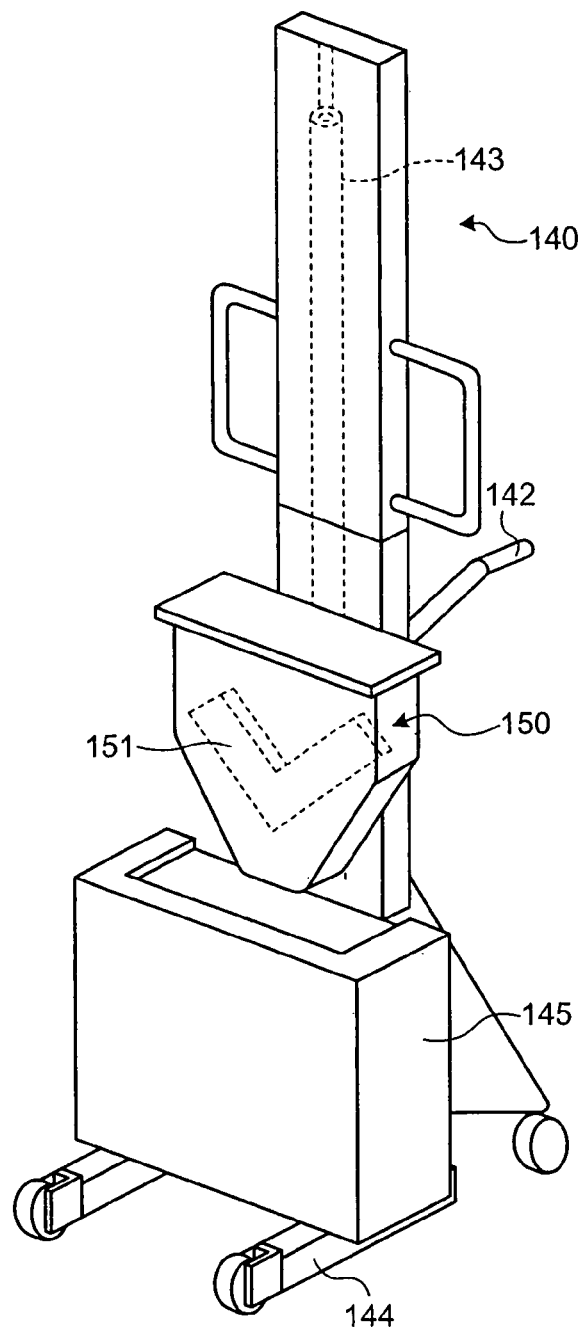
FIG. 32 is a diagrammatic perspective view showing an entire structure of the magnetic field generator 140 when used.

FIG. 31 is a diagrammatic perspective view showing an entire structure of a magnetic field generator 140 which is not in use and FIG. 32 is a diagrammatic perspective view showing an entire structure of the magnetic field generator 140 which is in use. The magnetic field generating unit 150 is fixed to an elevating unit 141 of the magnetic field generator 140 by the connection arm 157. The magnetic field generating unit 150 can be moved upward and downward via a chain 143 by operating an elevating handle 142. Further, when the magnetic field generating unit 150 is moved downwardly, the magnetic field generating unit 150 is configured to be contained in a magnet housing unit 145 having casters 144.

Figure 33:
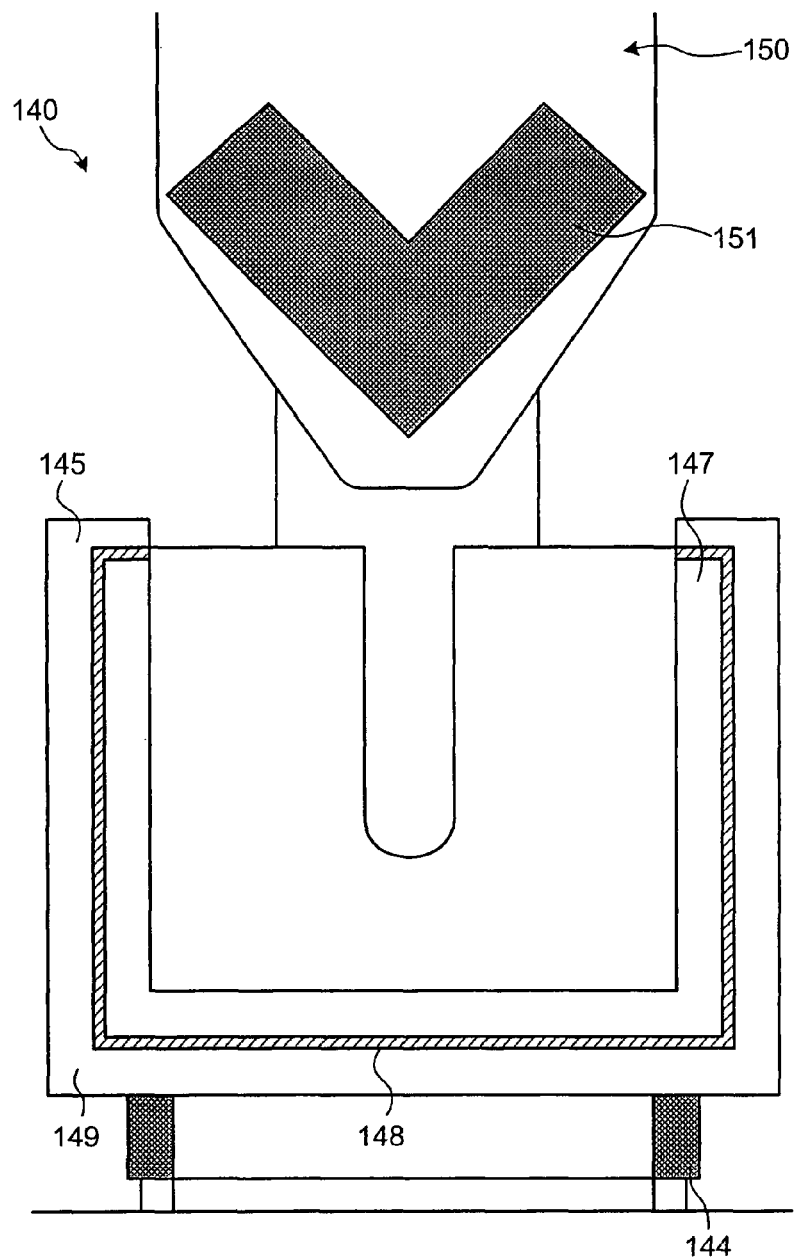
FIG. 33 is a front view showing a magnetic field generating unit 150 when used.
Figure 34:
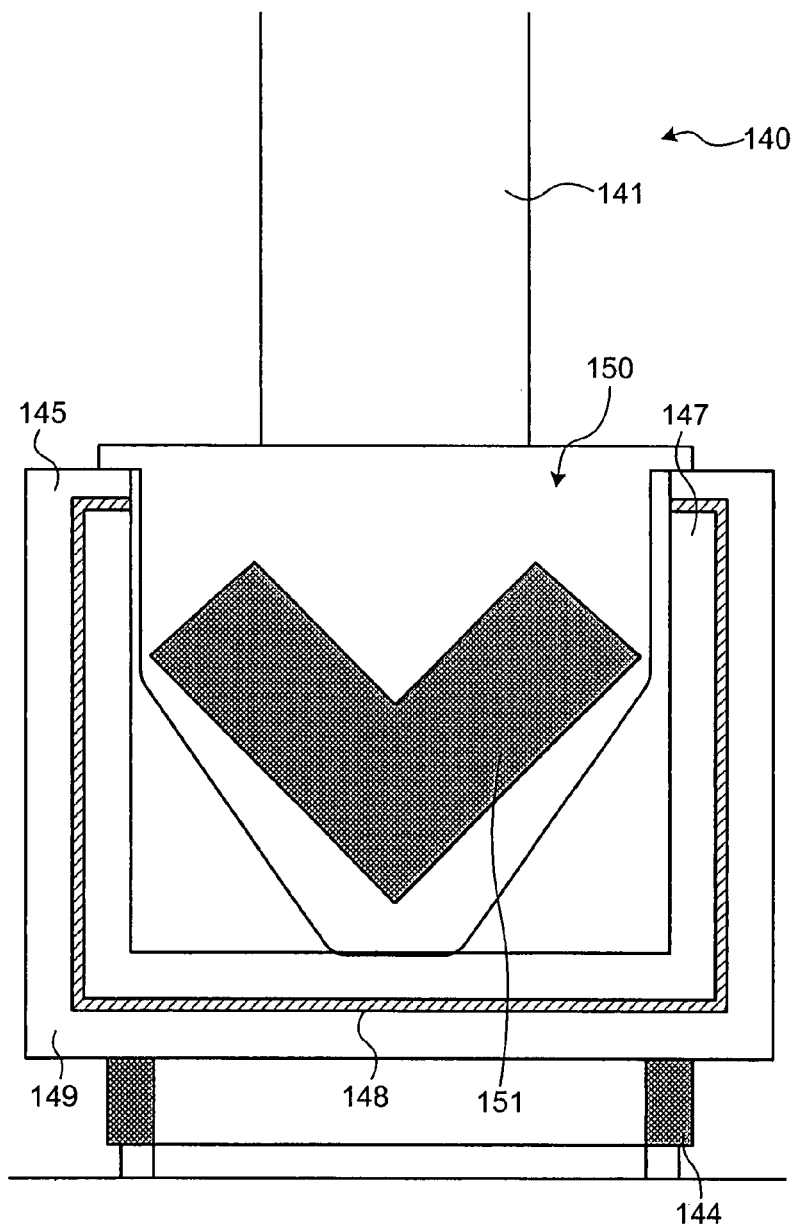
FIG. 34 is the front view showing a magnetic field generating unit 150 when not used.
Figure 35:
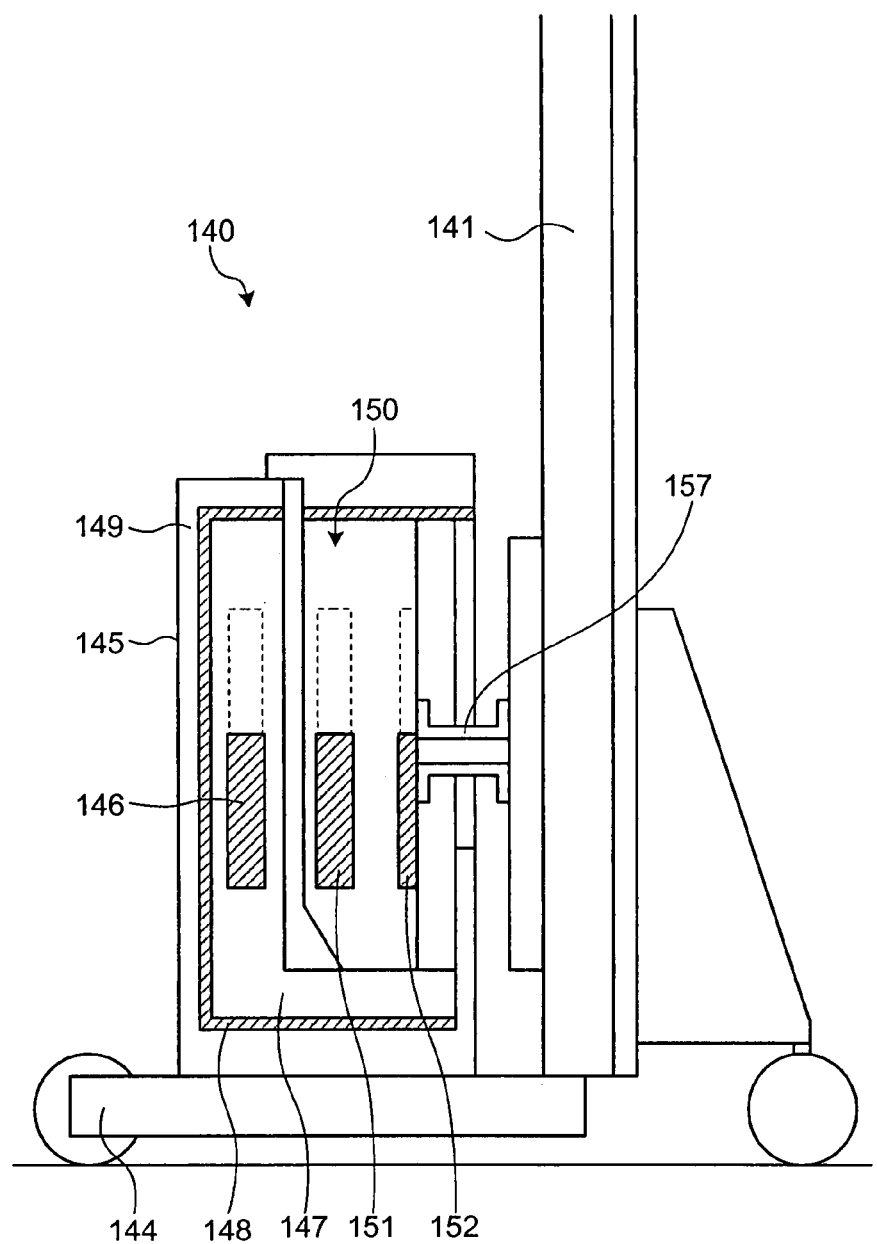
FIG. 35 is a longitudinal sectional side view showing the magnetic field generating unit 150 in FIG. 34.

Here, a relationship between the magnetic field generating unit 150 and the magnet housing unit 145 will be described with reference to FIGS. 33 to 35. FIG. 33 is a front view showing a magnetic field generating unit 150 when used, FIG. 34 is a front view showing the magnetic field generating unit 150 when not used, and FIG. 35 is a longitudinal sectional side view of the magnetic field generating unit 150 in FIG. 34. The magnetic field generating unit 150 is contained in the magnet housing unit 145 with a space thearearound and the cover 156 is formed so as to overlap the upper end of the magnet housing unit 145. Further, as shown in FIG. 35, when the magnetic field generating unit 150 is contained in the magnet housing unit 145, the magnetic material 146 formed in the same shape as the permanent magnet 151 is arranged in front of the permanent magnet 151 via a nonmagnetic material 147, and a magnetic material 148 and a nonmagnetic material 149 are alternatively disposed around these elements so as to reduce leakage of the magnetic field from the magnetic field generating unit 150.

Figure 36:
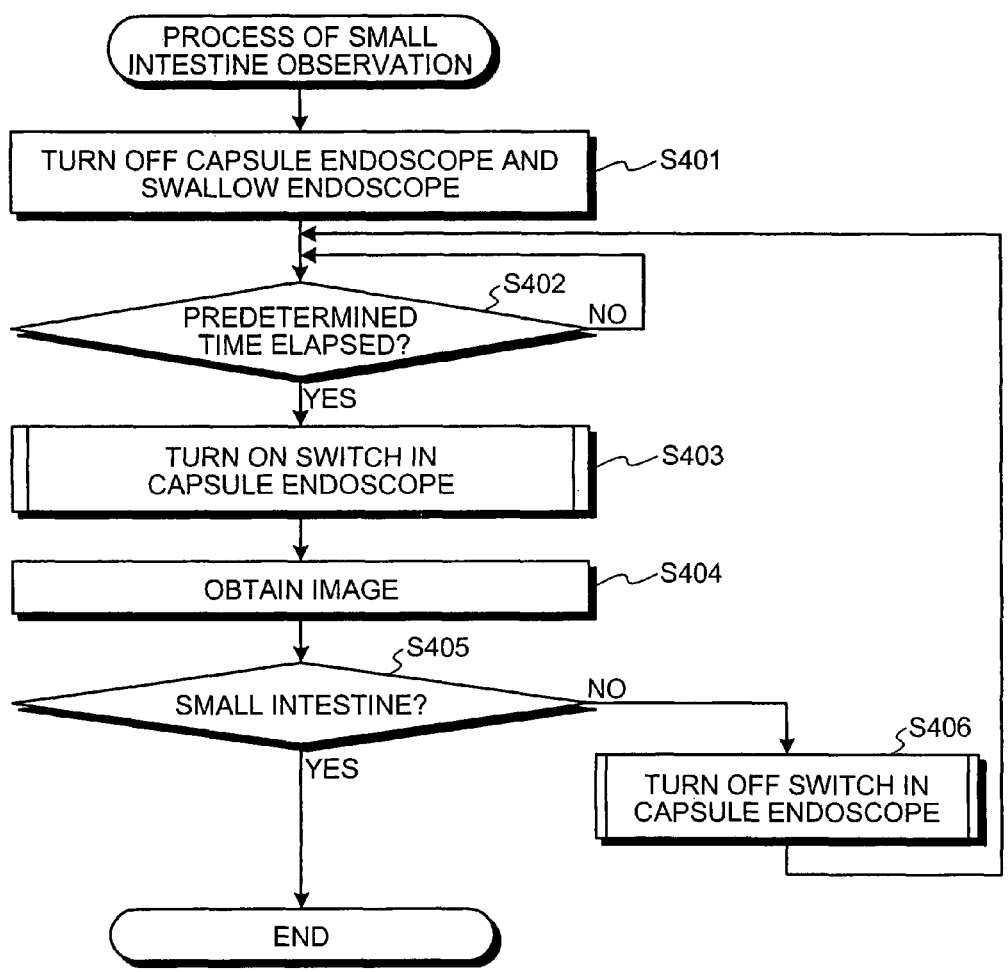
FIG. 36 is a flowchart showing a procedure for operating the capsule endoscope when the intra-subject medical system is used for a small intestine observation.

Next, a method of using the system to observe the small intestine will be described with reference to FIG. 36. In FIG. 36, firstly, functional units including the observation functional unit 12 in the capsule endoscope 2 is turned off and swallowed by a person to be examined (step S401). Then, it is determined whether or not a predetermined period of time has elapsed (step S403), and, only when the predetermined period of time has elapsed (step S402, Yes), a process of turning on is implemented to turn on the function switch in the capsule endoscope 2 (step S403, See FIG. 8). An image sent by the capsule endoscope 2 is received (step S404) and it is determined whether or not the image is an image showing the small intestine (step S405). When the small intestine is not shown in the image (step S405, No), a process of turning off is implemented to turn off the function switch in the capsule endoscope 2 (step S406, See FIG. 9), and then, the procedure goes back to step S402 to repeat the above procedure. On the other hand, when the small intestine is shown in the image (step S405, Yes), the procedure is completed. In this condition, the capsule endoscope 2 in the small intestine moves corresponding to peristaltic movements of the small intestine and sequentially takes images in the small intestine to send the images outside the subject 1. In this way, the large intestine can be observed.

It is noted that, in the first embodiment, the control of the on/off states of the observation functional unit 12 has mainly been described; however, the present invention is not limited to this and is applied to an on/off state control of each functional units when one or more functional units including a biopsy function, a medication function, a hemostatic function, a cauterization function and a marking function of the capsule endoscope 2. Further, in addition to the functional units, the present invention may be applied to an on/off state control of a part of functions of a radio transmission processing unit or the data processing/control unit 16. Further, the present invention may be applied to on/off state controls of not only objective functions but also general functions such as a locking function.

Next a second embodiment of the present invention will be described. According to the first embodiment, the magnetic field emission direction of the magnetic field generating unit 4 is controlled based on the information that is sent from capsule endoscope 2 and obtained by the viewer 6; however, according to the second embodiment, the magnetic field emission direction of the magnetic field generating unit 4 is controlled based on a position of the capsule endoscope 2.

Figure 37:
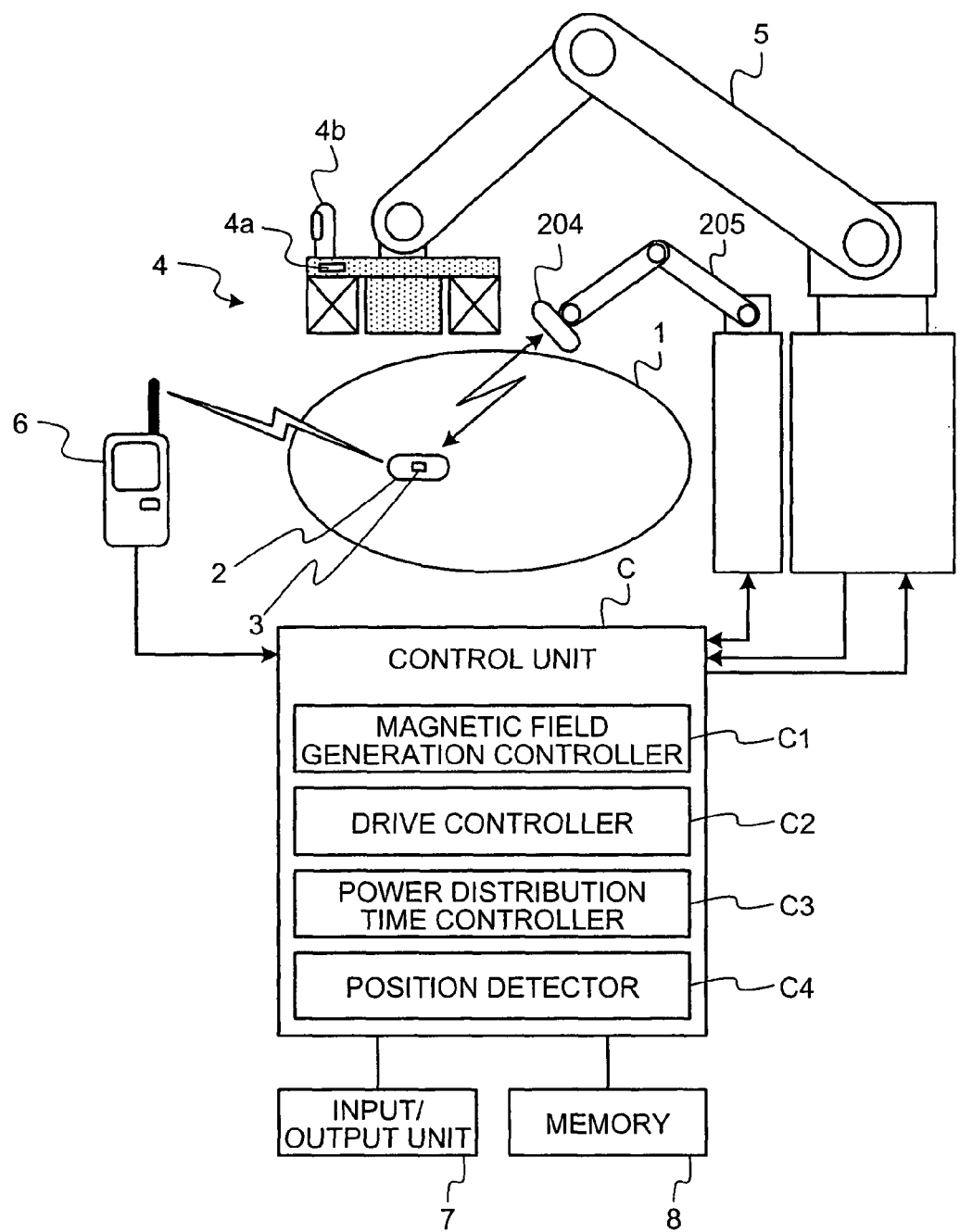
FIG. 37 is a view showing a general structure of an intra-subject medical system according to a second embodiment of the present invention.

FIG. 37 is a view showing a structure of an intra-subject medical system according to the second embodiment of the present invention. Compared to the intra-subject medical system of FIG. 1, this intra-subject medical system further includes a metal detector 204 for detecting the position of the capsule endoscope 2 by detecting the metal inside the capsule endoscope 2 such as a battery, an arm drive unit 205 for moving the metal detector 204 and a position detector C4 for detecting the position of the capsule endoscope 2 based on a detection result of the metal detector 204. The magnetic field generation controller C1 and the drive controller C2 control the magnetic field generation and emission direction of the magnetic field based on position information detected by the position detector C4. Since the position of the capsule endoscope 2 is already known, the region where the magnetic field generating unit 4 is moves is reduced and switching is implemented more quickly.

Figure 38:
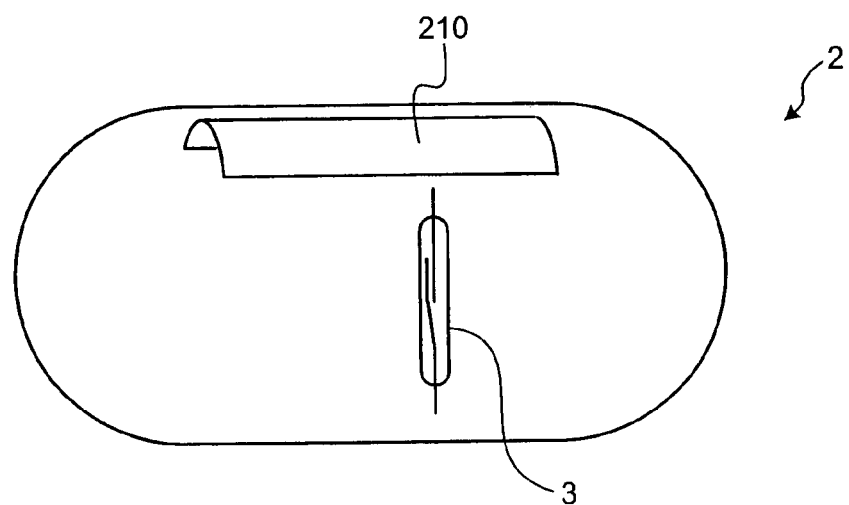
FIG. 38 is a view showing an example of a capsule endoscope in FIG. 37.

Here, as shown in FIG. 38, the capsule endoscope 2 preferably includes a magnetic sensor 3 so as to have directivity of detecting sensitivity in an axial direction of the capsule endoscope 2 and a conductive plate 210 having a face perpendicular to the detection sensitivity direction of the magnetic sensor 3. The metal detector 204 generates an eddy current on an conductive face of the conductive plate 210 and detects a magnetism generated by the eddy current. Accordingly, directivity is generated in a detection sensitivity of the metal detector 204 by creating a direction that generates a large eddy current by the conductive plate 210. As a result, the metal detector 204 recognizes that the axis of the capsule endoscope 2 is in a direction perpendicular to the direction of the large detection sensitivity so that a direction of the capsule endoscope 2 as well as the position of the capsule endoscope 2 can be detected. Thus, the region where the magnetic field generating unit 4 is moved is further reduced and switching can be implemented more quickly.

Figure 39:
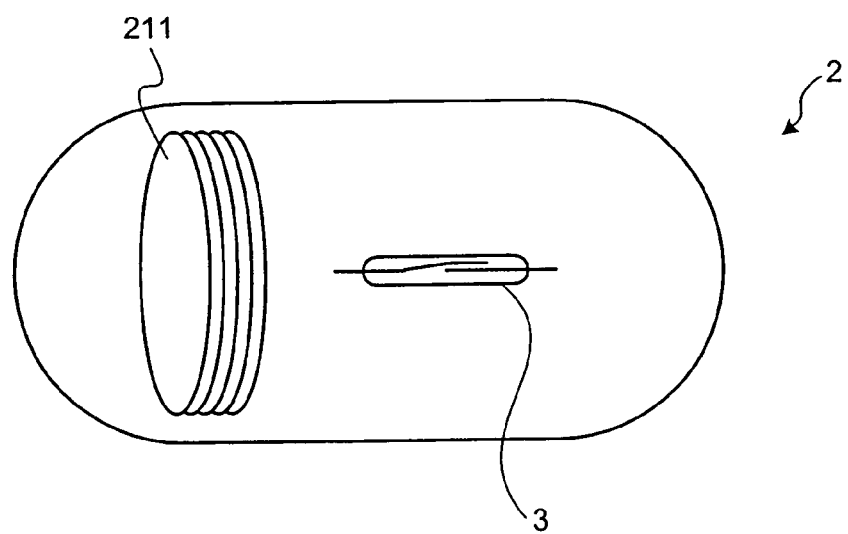
FIG. 39 is a view showing another example of the capsule endoscope in FIG. 37.

Further, as shown in FIG. 39, when the detection sensitivity direction of the magnetic sensor 3 is perpendicular to the axial direction of the capsule endoscope 2, the conductive face of the conductive plate 211 may be disposed perpendicular to the axial direction of the capsule endoscope 2.

It is noted that the conductive plates 210, 211 can be realized by a paramagnetic metal such as aluminum or copper that easily generates an eddy current.

Next, a third embodiment of the present invention will be described. According to the second embodiment, the conductive plate and metal detector are used for detecting the position of the capsule endoscope 2; however in the third embodiment, an LC marker is employed to detect the position of the capsule endoscope 2.

Figure 40:
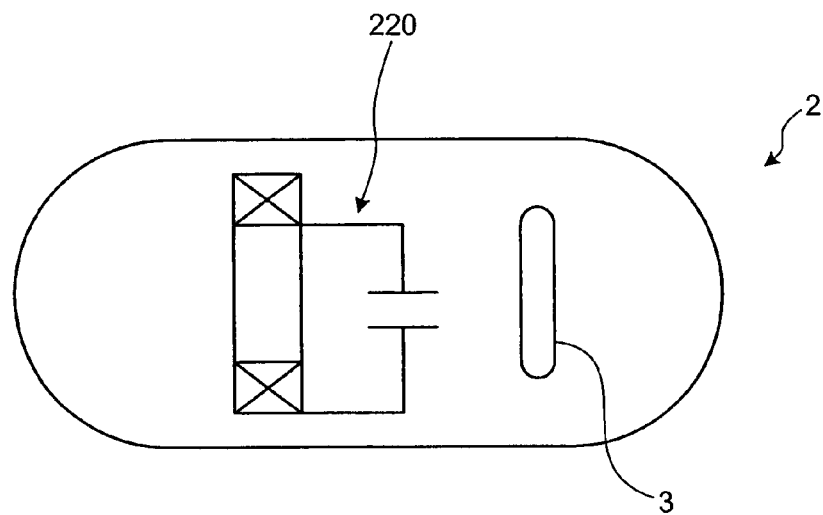
FIG. 40 is a view showing an example of a capsule endoscope employed in a third embodiment of the present invention.

As shown in FIG. 40, an LC marker 220 is provided in the capsule endoscope 2. The LC marker 220 is a resonance circuit connected to a coil and a condenser, receives an external alternate magnetic field in resonance frequency with the coil and generates an external alternate magnetic field from the coil by induced current accumulated in the condenser. In this case, the coil of the LC marker 220 has a directivity of magnetic field generation, so the direction of the capsule endoscope 2 as well as the position of the capsule endoscope 2 can be detected.

Figure 41:
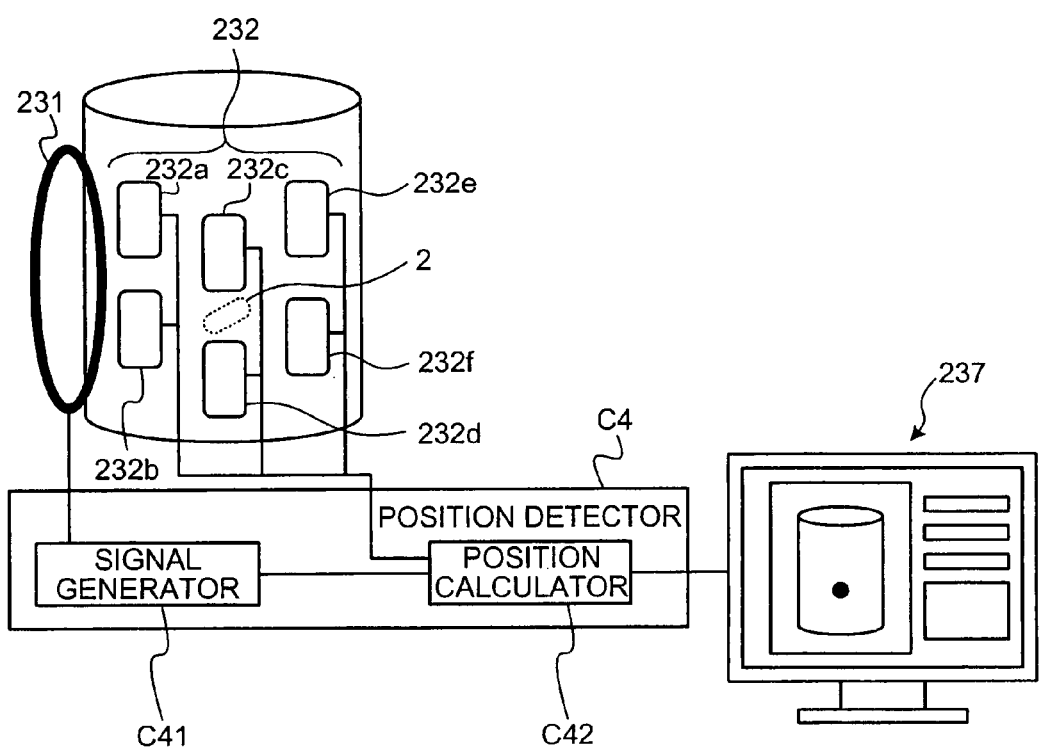
FIG. 41 is a view showing a structure of a position detection system of the intra-subject medical system according to the third embodiment of the present invention.

FIG. 41 is a view showing a structure of a position detection system using the LC marker 220. As shown in FIG. 41, the position detection system includes a drive coil 231 for generating an alternate magnetic field toward the LC marker 220 and a sense coil group 232 detecting the alternate magnetic field generated by the LC marker 220. The drive coil 231 and the sense coil group 232 are disposed on a surface of the subject 1. The position detector C4 includes a signal generating unit C41 for sending an alternate signal for instructing the drive coil 231 to generate an alternate magnetic field and a position calculator C42 for calculating the position of the capsule endoscope 2 based on the alternate magnetic field strength received by each sense coils 232a to 232f. The position calculated by the position calculator C42 is used for controlling movement of the magnetic field generating unit 4 or the like and, in this case, the calculated position may be output on a display unit 237, which is a part of the input/output unit 7.

According to the third embodiment using the LC marker 220, since power is not required by the LC marker 220, the position and direction of the capsule endoscope 2 can be detected even when the function switch of the capsule endoscope 2 is in an off-state.

Next, a fourth embodiment of the present invention will be described. According to the above-described second and third embodiments, the region where the magnetic field generating unit 4 is moved is reduced and switching is implemented quickly by detecting the position of the capsule endoscope 2; however, in the fourth embodiment, the direction of the capsule endoscope 2 is controlled and a magnetic field is emitted to the direction-controlled capsule endoscope 2.

Figure 42:
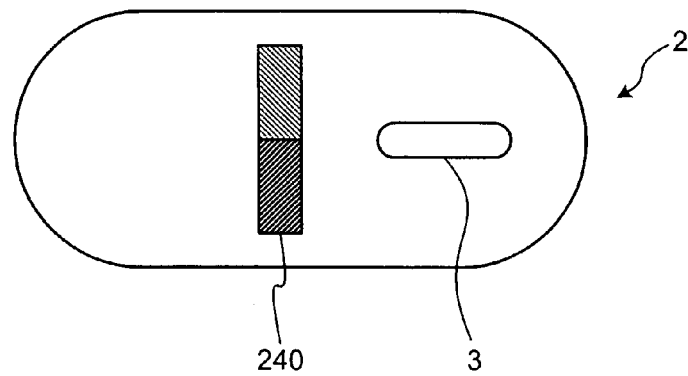
FIG. 42 is a vertical sectional view showing a capsule endoscope employed in a fourth embodiment of the present invention.
Figure 43:
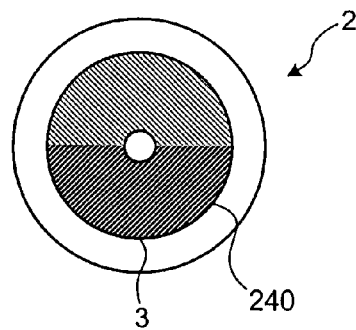
FIG. 43 is a transverse sectional view showing the capsule endoscope employed in the fourth embodiment of the present invention.
Figure 44:
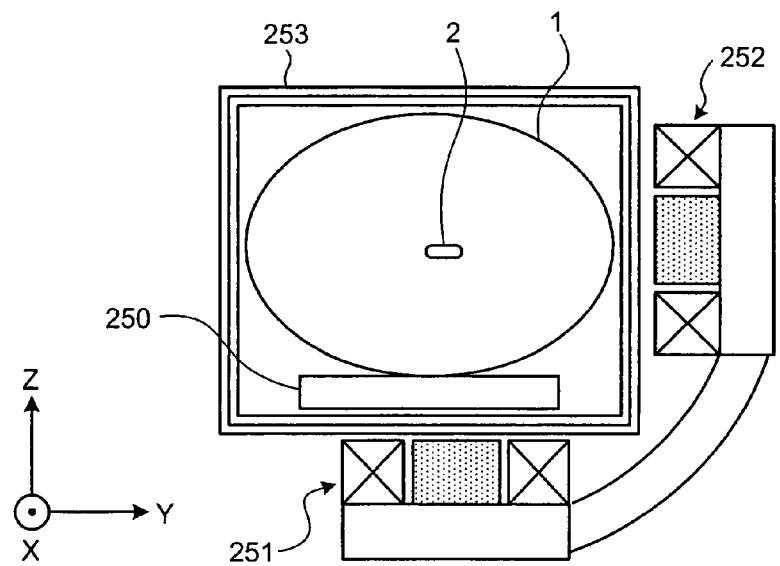
FIG. 44 is a view showing a structure of a position detection system of the intra-subject medical system according to the fourth embodiment of the present invention.

As shown in FIG. 42, the capsule endoscope 2 includes the magnetic sensor 3 along the axis of the capsule endoscope 2 and the magnetism detecting direction of the magnetic sensor 3 is directed parallel to the axis. Inside the capsule endoscope 2, a disk-shaped permanent magnet 240 for generating a magnetic field perpendicular to the axis and the surface of the permanent magnet 240 is placed perpendicular to the axis.

On the other hand, a magnetic field generating unit 251 for generating a magnetic field in a direction Z, a magnetic field generating unit 252 for generating a magnetic field in a direction Y and a magnetic field generating unit 253 for generating a magnetic field in a direction X are disposed around the subject 1. The subject 1 is placed on the mounting base 250 and its longitudinal direction is in the direction X.

Figure 45:
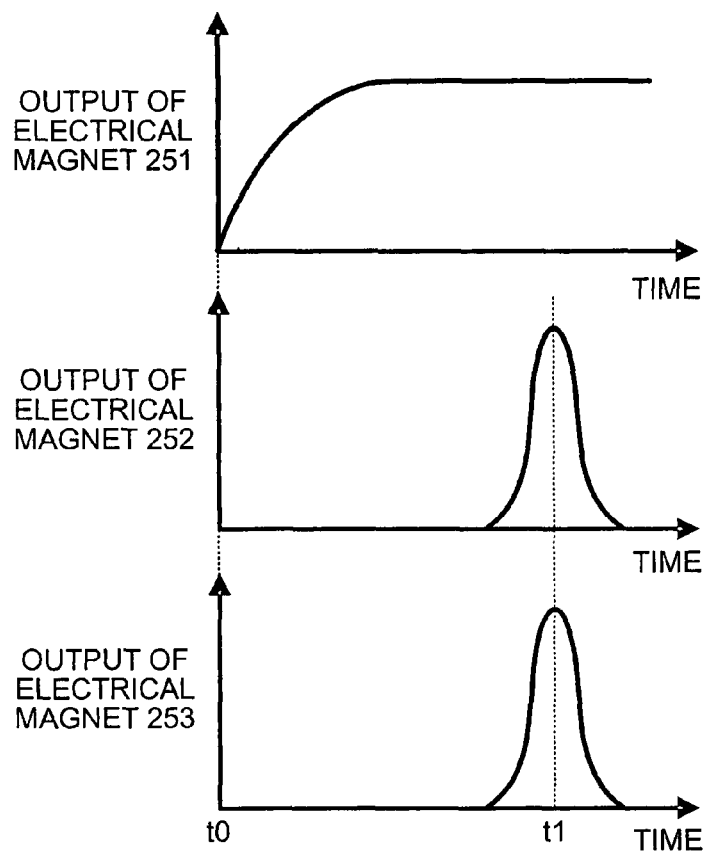
FIG. 45 is a view showing an on/off state control by the position detection system in FIG. 44.

As shown in FIG. 45, the magnetic field generating unit 251 generates a magnetic field to the subject 1 prior to the magnetic field generating units 252, 253 and when the longitudinal direction of the permanent magnet 240 directs the direction of the generated magnetic field, the axis of the capsule endoscope 2 is placed on the X-Y surface. That is, the magnetism detecting direction of the magnetic sensor 3 is placed on the X-Y surface. At a timing t1 as maintaining the magnetic field generation of the magnetic field generating unit 251 and the direction of the capsule endoscope 2, the magnetic field generating units 252, 253 emit temporary magnetic fields in the directions X and Y. With this, the magnetic sensor 3 is surely tuned on and the on/off state control of the function switch can be surely implemented.

Figure 46:
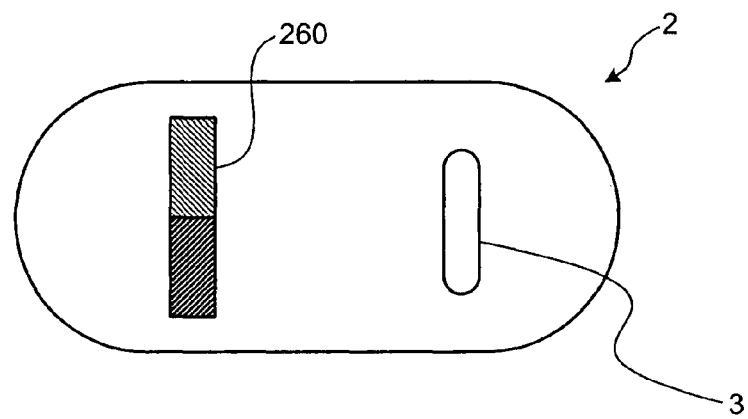
FIG. 46 is a view showing another example of the capsule endoscope according to the fourth embodiment of the present invention.

As shown in FIG. 46, the magnetic sensor 3 may be disposed so as to have a magnetism detecting direction perpendicular to the direction of the magnetic field generated by the permanent magnet 260 having the same structure and arrangement as the permanent magnet 240, that is, the axial direction of the capsule endoscope 2.

Next, a fifth embodiment of the present invention will be described. According to the above-described fourth embodiment, the magnetic sensor is turned on by controlling the direction of the capsule endoscope 2; however, in the fifth embodiment, an optical sensor 272 is employed as a substitute for the magnetic sensor 3.

Figure 47:
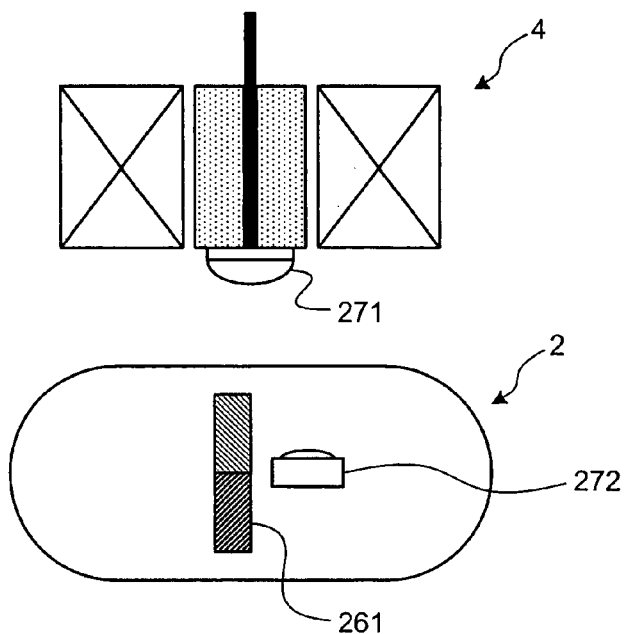
FIG. 47 is a view showing a structure of a capsule endoscope in an intra-subject medical system according to a fifth embodiment of the present invention.

As shown in FIG. 47, in the intra-subject medical system of the fifth embodiment, similar to the fourth embodiment, a permanent magnet 261 for controlling the posture is provided in the capsule endoscope 2. Similar to the fourth embodiment, the permanent magnet 261 is a flat plat forming a flat surface perpendicular to the axial direction of the capsule endoscope 2 and the magnetic field is perpendicular to the flat surface. The capsule endoscope 2 further includes an optical sensor 272 as a substitute for the magnetic sensor 3. The optical detecting direction of the optical sensor 272 is the same as the direction of the magnetic field of the permanent magnet 261. On the other hand, the magnetic field generating unit 4 includes an optical generating unit 271 such as an LED on its end.

When an on/off state control of the observation functional unit 12 in the capsule endoscope 2 is implemented, similar to the electrical magnet 251, a magnetic field is emitted from the magnetic field generating unit 4 to the subject 1 and the permanent magnet 261 is operated so as to change the posture of the capsule endoscope 4. In such condition, infrared light, for example, is emitted from the optical generating unit 271 to turn on the optical detector 272. In this case, according to the relation of the posture of the capsule endoscope 4 and the position of the magnetic field generating unit 4, the optical generating unit 271 and the optical detector 272 are facing each other and the optical detector 272 can surely be turned on. Based on the transfer to the on-state of the optical detector 272, the data processing/control unit 16 controls the on/off states of the functions in the observation functional unit 12.

Figure 48:
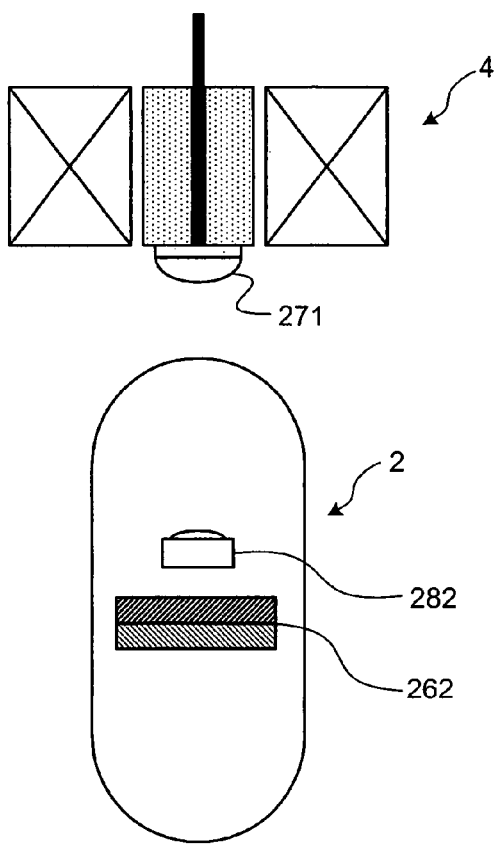
FIG. 48 is a view showing a structure of an example of the capsule endoscope in the intra-subject medical system according to the fifth embodiment of the present invention.

As shown in FIG. 48, a permanent magnet 262 may be provided as a substitute for the permanent magnet 261. The permanent magnet 262 is composed of layered disk-shaped North pole and South pole and disposed so that its flat face is perpendicular to the axis of the capsule endoscope 2. Further, an optical detector 282 having optical detecting direction in the axial direction of the capsule endoscope 2 is provided as a substitute for the optical detector 272. With such structure, the optical generating unit 271 and the optical detector 282 are faced each other so that the optical detector 282 can surely be turned on.

Next, a sixth embodiment of the present invention will be described. According to the fourth embodiment, the magnetic sensor is turned on by controlling the direction of the capsule endoscope 2; however, in the sixth embodiment, a conductive plate is provided as a substitute for the permanent magnet to control the direction of the capsule endoscope 2.

Figure 49:
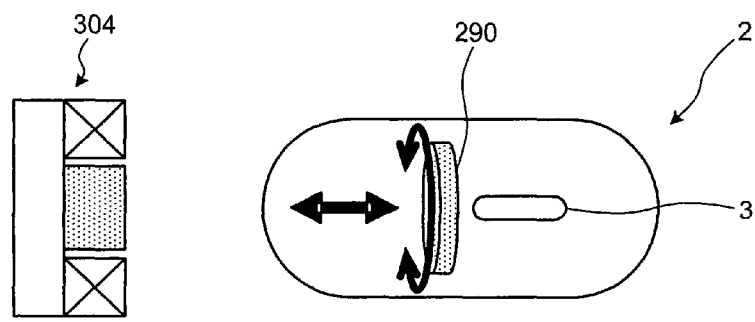
FIG. 49 is a view showing a structure of a capsule endoscope in an intra-subject medical system according to a sixth embodiment of the present invention.

In other words, as shown in FIG. 49, the magnetic sensor 3 is disposed so that the magnetic field detecting direction of the magnetic sensor 3 is perpendicular to the axis of the capsule endoscope 2 and a disk-shaped conductive plate 290 formed by metal such as aluminum or copper is provided. In this case, a plate surface of the conductive plate 290 is disposed perpendicular to the axis of the capsule endoscope 2.

Figure 50:
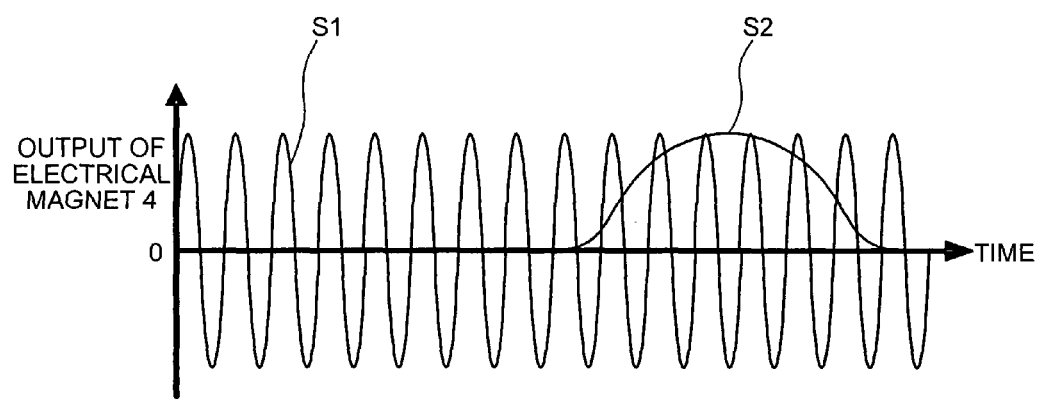
FIG. 50 is a view showing an on/off state control by the capsule endoscope in FIG. 49.

When the on/off state control of the observation functional unit 12 in the capsule endoscope 2 is implemented, firstly as shown in FIG. 50, an alternate-current magnetic field S1 of several tens of kHz is generated from the magnetic field generating unit 304. On the conductive plate 290, an eddy current corresponding to the alternate-current magnetic field is generated and the conductive plate 290 is magnetized by the eddy current. Accordingly, since the alternate-current magnetic field of the magnetic field generating unit 304 and the magnetic field of the conductive plate 290 are synchronized, the direction of the capsule endoscope 2 is controlled by the direction of the magnetic field of the magnetic field generating unit 304. In such condition, the a temporary magnetic field S2 is emitted, for example, from the magnetic field generating unit 4, in a direction perpendicular to the axis of the capsule endoscope 2. With this, the magnetic sensor 3 is turned on and, based on the transfer to the on-state of the magnetic sensor 3, the data processing/control unit 16 controls the on/off states of the functions of the observation functional unit 12.

The resonance frequency of the magnetic sensor 3 is set smaller than the frequency of the alternate-current magnetic field generated by the magnetic field generating unit 304 (see FIG. 50). With such setting, a chattering of the magnetic sensor 3 generated by the alternate-current magnetic field can be prevented.

Next, a seventh embodiment of the present invention will be described. According to the fourth embodiment, the magnetic sensor is turned on by controlling the direction of the capsule endoscope 2; however, in the sixth embodiment, a ferromagnetic material bar is provided as a substitute for the permanent magnet to control the direction of the capsule endoscope 2.

Figure 51:
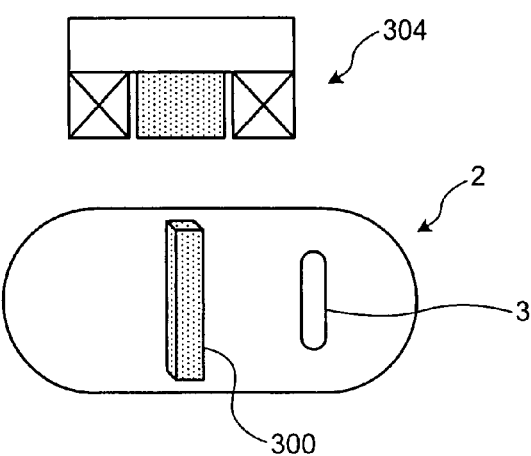
FIG. 51 is a view showing a structure of a capsule endoscope in an intra-subject medical system according to a seventh embodiment of the present invention.

In other words, as shown in FIG. 51, the magnetic sensor 3 is disposed so that the magnetic field detecting direction of the magnetic sensor 3 is to be the axial direction of the capsule endoscope 2 and a ferromagnetic material bar 300 is provided, whose longitudinal direction is to be perpendicular to the axis of the capsule endoscope 2.

When controlling the on/off states of the observation functional unit 12 in the capsule endoscope 2, firstly, a magnetic field is generated from the magnetic field generating unit 304 to the subject 1. The ferromagnetic material bar 300 is magnetized by the magnetic field emitted by the magnetic field generating unit 3 and the posture of the capsule endoscope 2 is controlled so that the longitudinal direction directs in the same direction of the magnetic field direction. In such condition, a temporary magnetic field is emitted from, for example, the magnetic field generating unit 4 in the axial direction of the capsule endoscope 2. With this, the magnetic sensor 3 is turned on and, based on the transfer to the on-state of the magnetic sensor 3, the data processing/control unit 16 controls the on/off states of the functions of the observation functional unit 12.

Since the ferromagnetic material bar 300 does not generate magnetism, the magnetic sensor 3 and the ferromagnetic material bar 300 may be arranged closed to each other in the capsule endoscope 2. Accordingly, the design of the capsule endoscope 2 becomes more flexible.

Next, an eighth embodiment of the present invention will be described. According to the first embodiment, the on/off states of the observation functional unit 12 is controlled by the magnetic sensor 3; however, in the eighth embodiment, a temperature sensor, as a substitute for the magnetic sensor 3, for detecting a heat generated by a magnetism to indirectly detect the magnetism.

Figure 52:
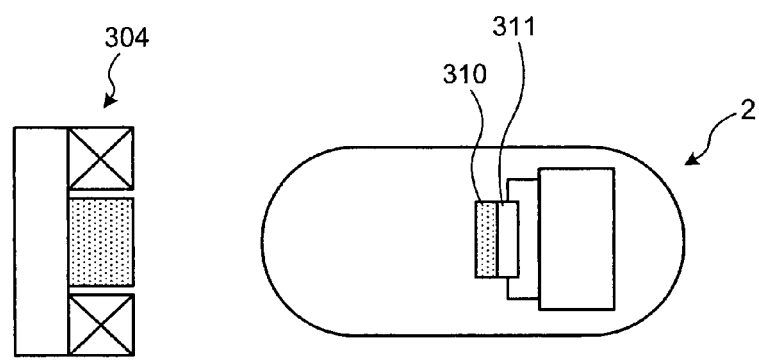
FIG. 52 is a view showing a structure of a capsule endoscope in an intra-subject medical system according to an eighth embodiment of the present invention.

In other words, as shown in FIG. 52, a heat generator 310 for generating heat by an induction heating and a temperature sensor 311 for detecting the temperature resulting from the heat generated by the heat generator 310 are provided in the capsule endoscope 2. When an alternate-current magnetic field is emitted from the external magnetism generating unit 304, the heat generator 310 generates heat according to the magnetic field strength and the temperature sensor 311 detects the temperature resulting from the heat. When the temperature becomes equal to or greater than a predetermined value, the data processing/control unit 16 controls the on/off states of the observation functional unit 12.

Next, a ninth embodiment of the present invention will be described. According to the first embodiment, the on/off states of the observation functional unit 12 is controlled by the magnetic sensor 3; however, in the eighth embodiment, an X-ray is used as a physical quantity and when an X-ray sensor disposed in the capsule endoscope detects an X-ray, the on/off states of the observation functional unit 12 is controlled.

Figure 53:
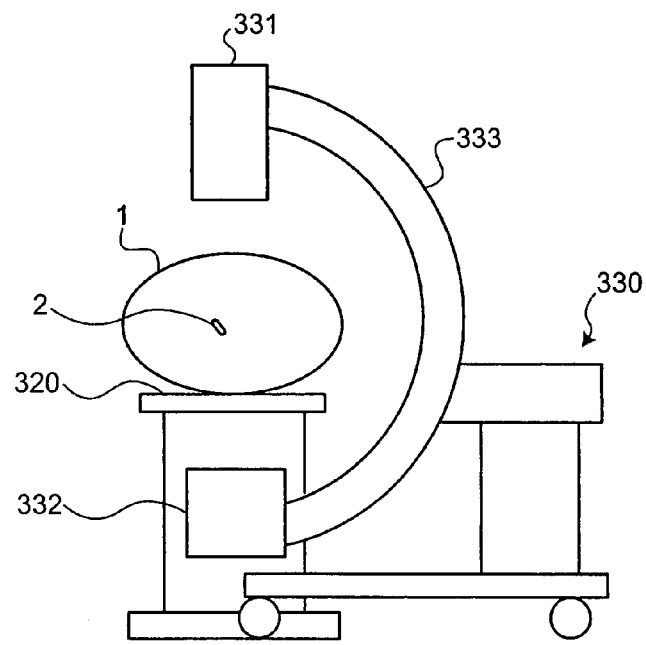
FIG. 53 is a view showing a structure of an X-ray emission imaging device in an intra-subject medical system according to a ninth embodiment of the present invention.
Figure 54:
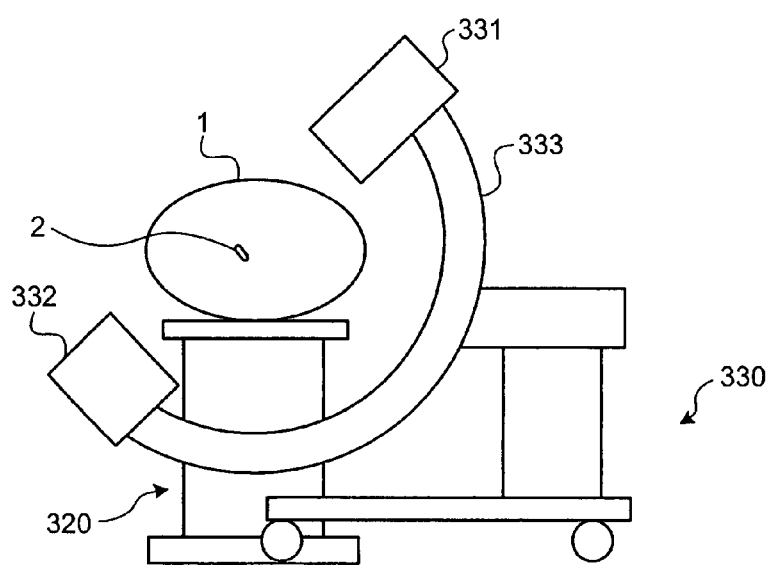
FIG. 54 is a view showing a condition during movement of the X-ray emission imaging device in the intra-subject medical system according to the ninth embodiment of the present invention.
Figure 55:
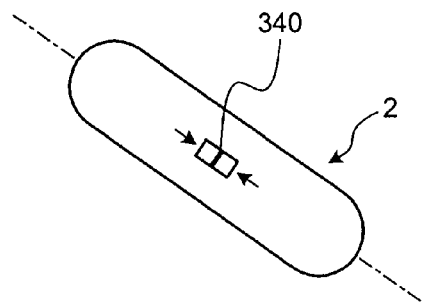
FIG. 55 is a view showing a structure of a capsule endoscope in the intra-subject medical system according to the ninth embodiment of the present invention.

FIGS. 53 and 54 are views showing general structures of the ninth embodiment of the present invention, and FIG. 55 is a view schematically showing structure of a capsule endoscope according to the ninth embodiment of the present invention. In FIG. 53, the intra-subject medical system includes an X-ray emission imaging device 330. The X-ray emission imaging device 330 includes an X-ray emitting unit 331 and an X-ray receiving unit 332 which are arranged facing each other. As shown in FIG. 54, the facing X-ray emitting unit 331 and an X-ray receiving unit 332 can be rotated and moved while maintaining the positional relationship. Further, a mounting base 320 is provided so that the subject 1 is placed between those facing X-ray emitting unit 331 and an X-ray receiving unit 332.

When the on/off states of the observation functional unit 12 in the capsule endoscope 2 is controlled, firstly, a weak X-ray is emitted from the X-ray emitting unit 331 to the subject 1 and an X-ray image of the capsule endoscope 2 is obtained. Then, the X-ray emitting unit 331 and an X-ray receiving unit 332 are moved to emit the weak X-ray to the subject 1 from a different direction and an X-ray image of the capsule endoscope 2 is obtained. The position and posture of the capsule endoscope 2 are calculated based on the two X-ray images. According to the calculated position and posture, the X-ray emitting unit 331 and an X-ray receiving unit 332 are moved and a strong X-ray is temporarily emitted from, for example, the axial direction of the capsule endoscope 2 and the X-ray sensor 340 in the capsule endoscope 2 is securely turned on. Based on the transfer to the on-state of the X-ray sensor 340, the data processing/control unit 16 controls the on/off states of the observation functional unit 12.

As shown in FIG. 55, the X-ray sensor 340 is disposed so as to have sensitivity in the axial direction of the capsule endoscope 2. The X-ray sensor 340 is composed of an X-ray sensor having sensitivity in an axial direction and an X-ray sensor having sensitivity in another axial direction and those sensors are arranged back-to-back. Accordingly the X-ray sensor 340 is configured to surely detect X-rays emitted in either one of the axial directions.

Next, a tenth embodiment of the present invention will be described. According to the first to ninth embodiments, a single physical quantity detecting member such as a magnetic sensor is provided; however, in the tenth embodiment, a plurality of physical quantity detecting members are provided to control the on/off states of a plurality of observation functional units.

Figure 56:
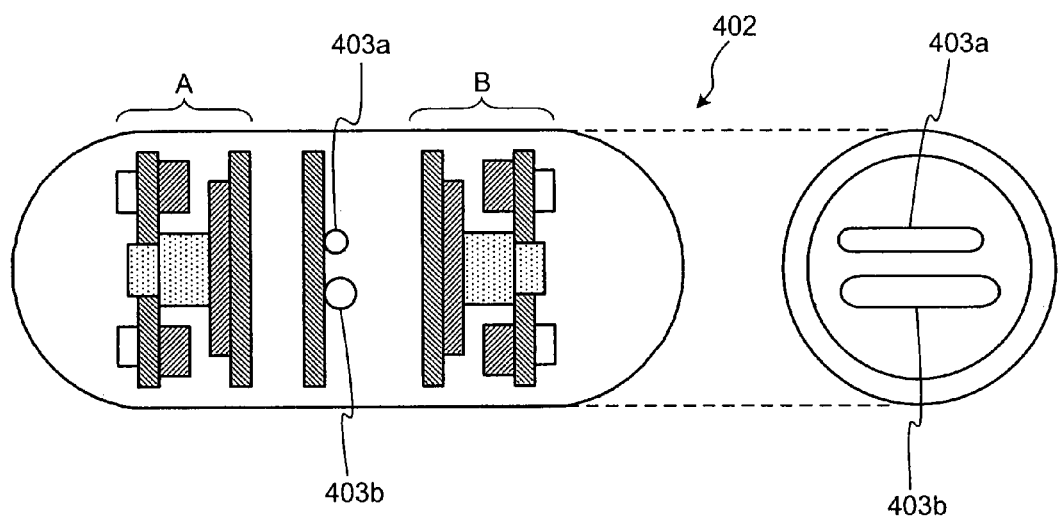
FIG. 56 is a view showing a structure of a capsule endoscope in an intra-subject medical system according to a tenth embodiment of the present invention.
Figure 57:
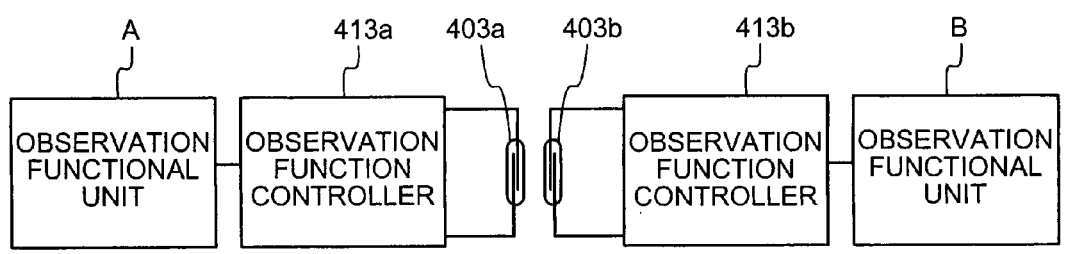
FIG. 57 is a block diagram showing a structure of the capsule endoscope in FIG. 56.
Figure 58:
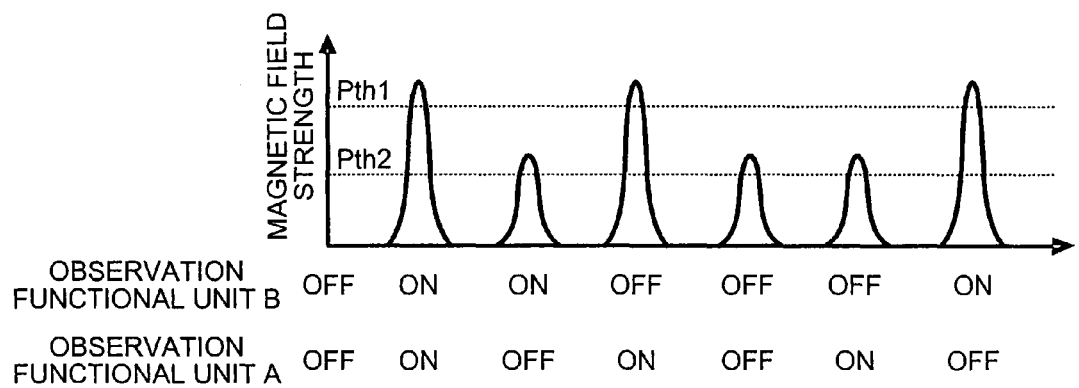
FIG. 58 is a view showing an example of an on/off state control for the capsule endoscope in FIG. 56.

FIG. 56 is a schematic view showing a general structure of a capsule endoscope according to a tenth embodiment of the present invention. FIG. 57 is a block diagram showing a structure, in the capsule endoscope in FIG. 56, for controlling an on/off states of an observation functional unit. FIG. 58 is a view showing a relationship between an external magnetic field strength and on/off states when the on/off states of two observation functional units are controlled by an external magnetic field.

In FIGS. 56 to 58, the capsule endoscope 402 includes therein two observation functional units A, B, observation control units 413a, 413b for controlling on/off states of the observation functional units A, B, and two magnetic sensors 403a, 403b. The magnetic sensor 403a is a magnetism switch turned on or off by a weak magnetic field strength Pth2 and the magnetic sensor 403b is a magnetism switch turned on or off by a magnetic field Pth1 which is greater than the magnetic field strength Ph2. Other structures are the same as those of the intra-subject medical system shown in FIG. 1.

A procedure of selectively controlling an on/off states of one of or both of the observation functional units A, B in the capsule endoscope 2 will be described. In the tenth embodiment, the on/off states of the magnetic sensor is the same as the on/off states of the observation control units 413a, 413b. Firstly, in order to switch both of the observation functional units A, B from an off-state to an on-state, a magnetic field greater than the magnetic field strength Pth1 is emitted from the magnetic field generating unit 4. In order to switch only the observation functional unit A from an off-state to an on-state, a magnetic field smaller than the magnetic field strength Pth1 and greater than the magnetic field strength Pth2 is emitted from the magnetic field generating unit 4. In order to switch only the observation functional unit B to an on-state, a magnetic field greater than the magnetic field strength Pth1 is emitted to turn on both of the observation functional units A, B, and then, a magnetic field smaller than the magnetic field strength Pth1 and greater than the magnetic field strength Pth2 is emitted to turn off the observation functional unit A and on the observation functional unit B. Or, a magnetic field smaller than the magnetic field strength Pth1 and greater than the magnetic field strength Pth2 is emitted to turn on only the observation functional unit A, and then, a magnetic field greater than the magnetic field strength Pth1 is emitted to turn off the observation functional unit A and on the observation functional unit B.

In other words, as shown in FIG. 58, in order to switch the current on/off states of both of the observation functional units A, B, a magnetic field greater than the magnetic field strength Pth1 is emitted. In order to switch the current on/off states of the observation functional unit A, a magnetic field smaller than the magnetic field strength Pth1 and greater than the magnetic field strength Pth2 is emitted. With use of the combination of these, desired on/off states can be realized.

According to the system in the tenth embodiment, the on/off states of the plurality of observation functional units are independently controlled by using a single magnetic field as a physical quantity.

Figure 59:
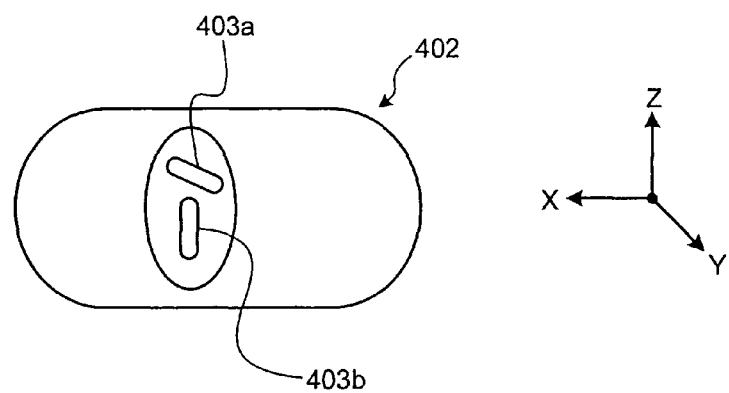
FIG. 59 is a view showing another structure of the capsule endoscope in the intra-subject medical system according to the tenth embodiment of the present invention.

The above-described magnetic sensors 403a, 403b are configured to detect magnetism with various magnetic field strengths; however, the present invention is not limited to this and, for example, magnetic sensors having different resonance frequency may be employed, or, as shown in FIG. 59, a plurality of magnetic sensors may be arranged so as to detect magnetism in different directions.

Further, according the above-described system, a physical quantity is realized as a magnetic field; however, the present invention is not limited to this and an optical sensor, an X-ray sensor and the like may be combined to control the on/off states independently. In this case, different physical quantity generating members are required if different sensors are employed in combination.

According to the first to tenth embodiments, the on/off state control of the observation functional unit has mainly been explained; however, the present invention is not limited to this and it may be applied to an on/off state control of a plurality of functional units such as radio transmission function, medicinal solution release function, marking function, bodily fluid/tissue sampling function, or operation arm function. Obviously, it may be applied to system having a plurality of same functional units.

Further, according to the first to tenth embodiments, a magnetic field, light such as an infrared ray, and corpuscular ray such as X-ray are described as examples of the physical quantity; however, the present invention is not limited to this and, for example, it may be applied to physical quantities such as radio transmission and sound wave. Here, a physical quantity detecting member in a capsule endoscope is assumed to have a directivity to detect a physical quantity.

A case in which the intra-subject medical system including the above-described capsule endoscope 2 is applied to an endoscopic surgical operation will be explained.

Figure 60:
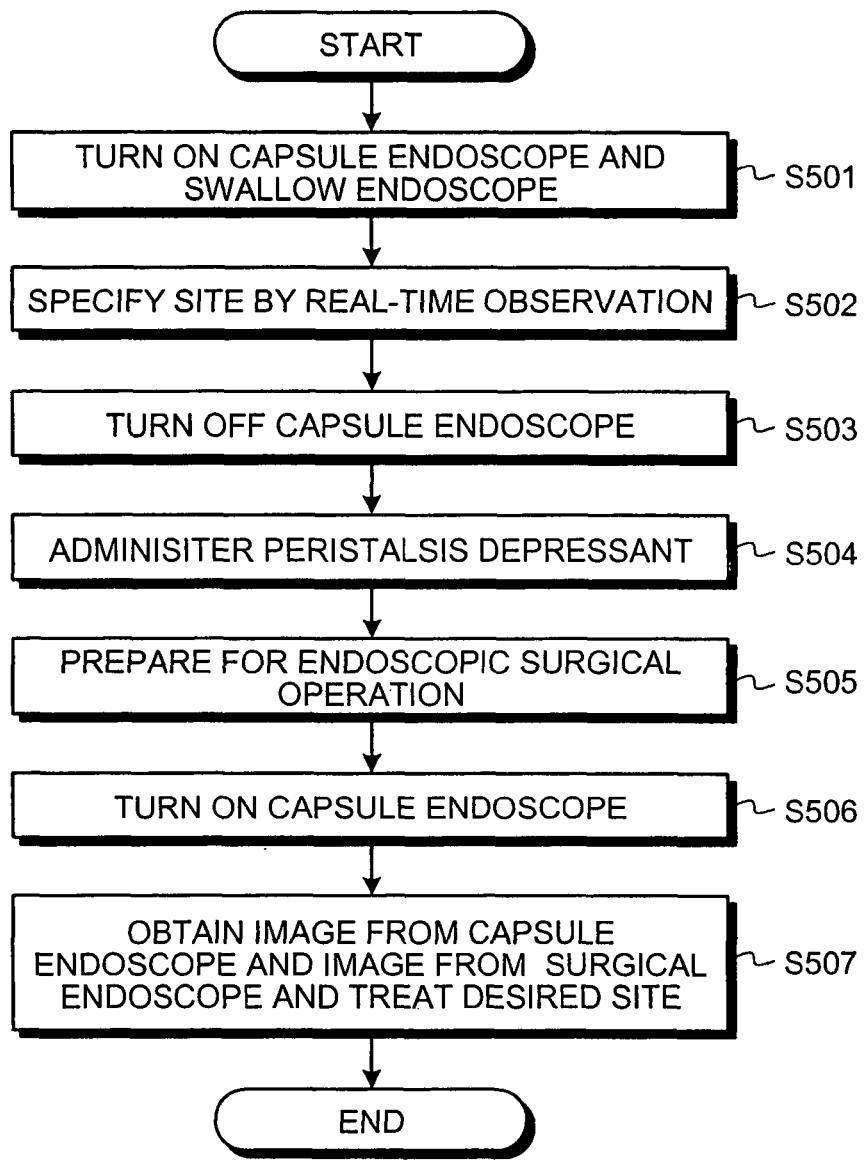
FIG. 60 is a flowchart showing a procedure of a first application example of the intra-subject medical system.

A first application example will be described. FIG. 60 is a flow chart showing a procedure of a first application example of the intra-subject medical system applied to an endoscopic surgical operation. Firstly, the capsule endoscope 2 is turned on and swallowed by a patient (step S501). Then, a site to be treated is specified in a real-time observation using the observation functional unit 12 (step S502). The capsule endoscope 2 is turned off (step S503). Further a depressant is administrated to the patient (step S504). This peristalsis depressant is administrated to prevent the capsule endoscope 2 from moving away from the specific site by peristalsis.

Then, a preparation for an endoscopic surgical operation is performed (step S505), and when the preparation is completed, the capsule endoscope 2 is turned on (step S506). An image from the capsule endoscope and an image from a surgical endoscope are obtained and the desired specific site is treated while monitoring the images (step S507). Then, the procedure is completed.

Figure 61:
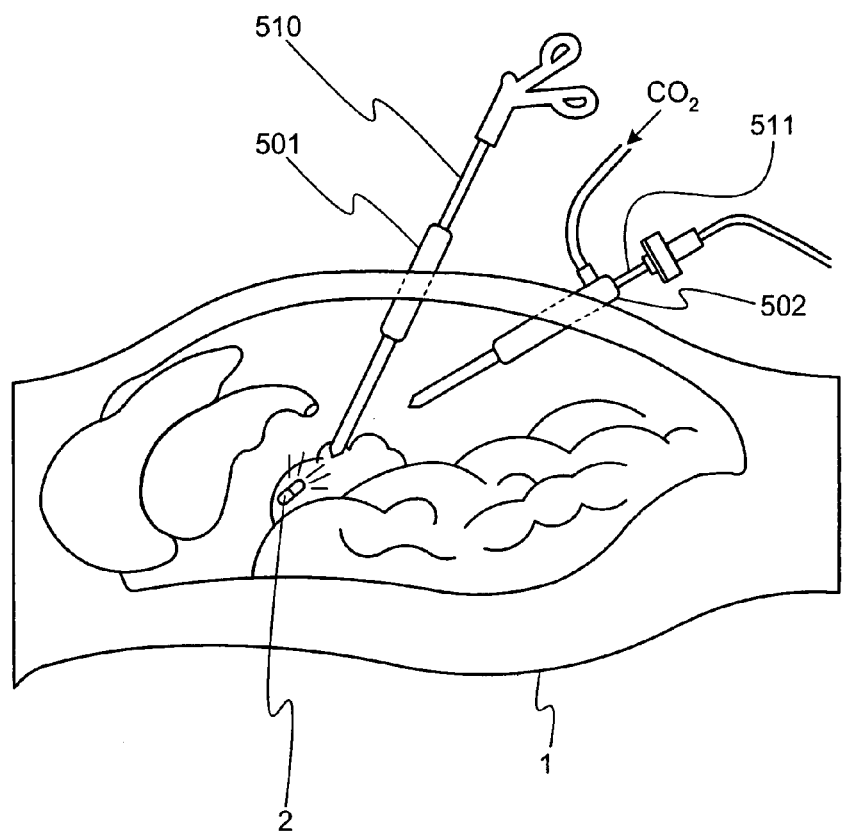
FIG. 61 is a view showing an outline of an endoscopic surgical operation.

Here, the endoscopic surgical operation is, as shown in FIG. 61, to form an abdominal cavity by introducing carbon dioxide into the patient body and to implement, in this condition, a surgical operation using an endoscope 511 or a forceps 510 and a surgical operation can be performed with a small cut for forming a forcep hole 501 or the like. According to the first application example, an image inside the digestive canal can be monitored, more definitive treatment can be performed. Further, the electricity consumption of the capsule endoscope 2 can be reduced. A similar effect may be obtained in general abdominal operations or the like as well as the endoscopic surgical operation.

According to the first application example, a desired site is specified in a real-time observation in step S502; however, the present invention is not limited to this and the desired site may be automatically specified by implementing a predetermined image process on an obtained image. For example, when an image includes a larger red area, it may be determined as the desired site. After the desired site is specified, the capsule endoscope 2 is automatically turned off by controlling the magnetic field generating unit 4.

Figure 62:
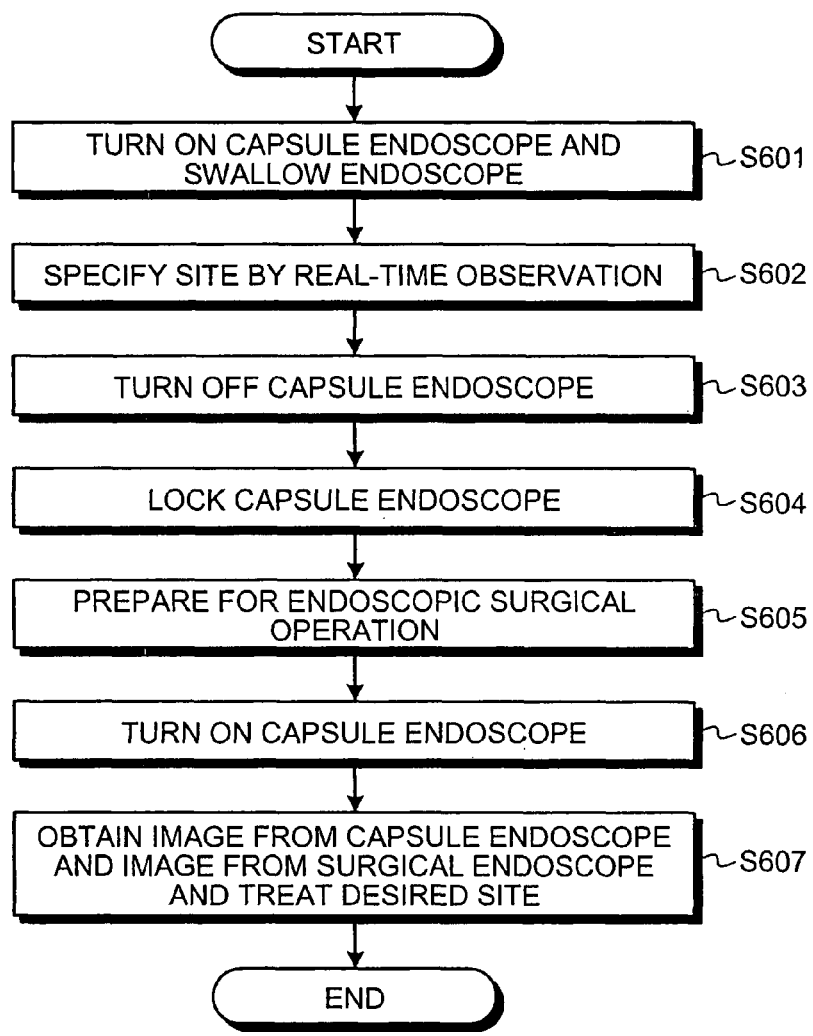
FIG. 62 is a flowchart showing a procedure of a second application example of the intra-subject medical system.

Next, a second application example will be described. As shown in FIG. 62, in the second application example, the capsule endoscope 2 is locked by turning on a locking function unit of the capsule endoscope 2 (step S604), as a substitute for administering a peristalsis depressant in the first application example (step S504). Other constituents, steps S601 to S603 and S605 to S607, are the same as steps S501 to S503 and S505 to S507 in FIG. 60.

Figure 63:
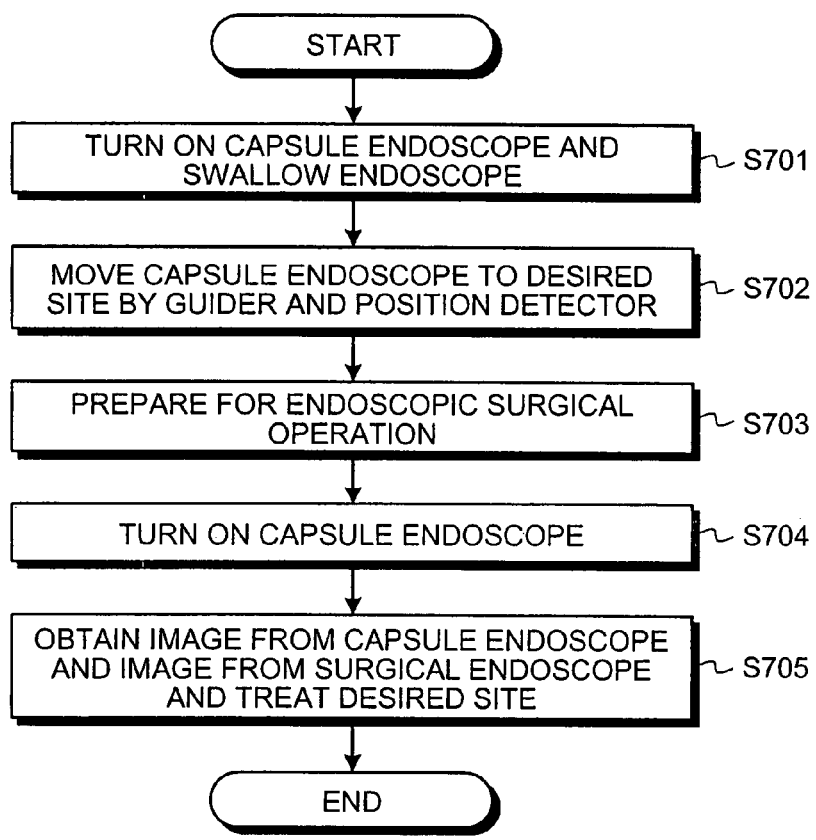
FIG. 63 is a flowchart showing a procedure of a third application example of the intra-subject medical system.

Next a third application example will be described. As shown in the flow chart in FIG. 63, in the third application example, firstly, the capsule endoscope 2 is turned off and swallowed by a patient (step S701). Then, the capsule endoscope 2 is moved to a desired site with use of a guiding member and a position detecting member described in the above embodiments (step S702).

Figure 64:
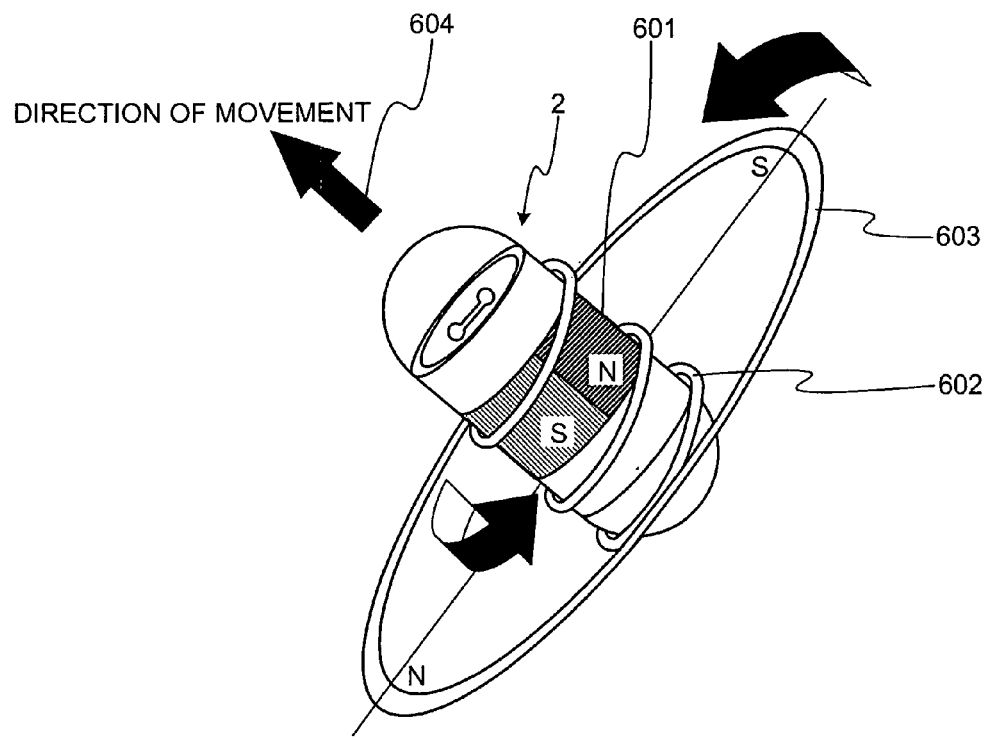
FIG. 64 is a view showing a general structure of a guiding member.

Here, the guiding member is, for example, to move the capsule endoscope 2 in an axial direction 604 by adding a rotational magnetic field from outside the subject 1, while a spiral member 602 is provided around the capsule endoscope 2 and a permanent magnet forming a magnetic field perpendicular to the axis of the capsule endoscope 2 is provided therein, as shown in FIG. 64.

Then, a preparation for an endoscopic surgical operation is performed (step S703) and, when the preparation is completed, the capsule endoscope 2 is turned on (step S704). Then, an image from the capsule endoscope and an image from a surgical endoscope are obtained and the desired specific site is treated while monitoring the obtained images (step S705). Then, the procedure is completed.

In the third application example, the power source energy of the capsule endoscope 2 can be preserved since the capsule endoscope 2 is kept in an off-state until the endoscopic surgical operation is started.

Figure 65:
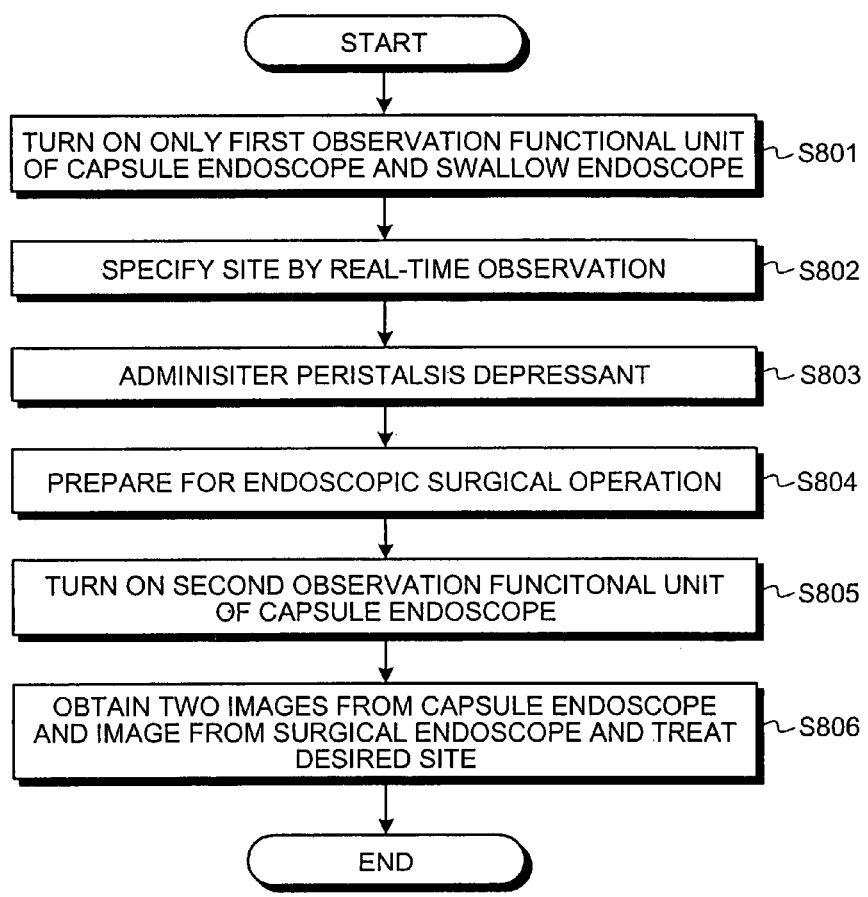
FIG. 65 is a flowchart showing a procedure of a fourth application example of the intra-subject medical system.

Next, a fourth application example will be described. In the fourth application example, two observation functional units are assumed to be included. As shown in the flow chart in FIG. 65, in the fourth application example, firstly only a first observation functional unit of the capsule endoscope 2 is turned on and the capsule endoscope 2 is swallowed by a patient (step S801). Then, a desired site is specified in a real-time observation using the first observation functional unit (step S802). A peristalsis depressant is administrated to the patient (step S803).

A preparation for an endoscopic surgical operation is performed (step S804), and, when the preparation is completed, a second observation functional unit of the capsule endoscope 2 is turned on (step S805). Two images from the capsule endoscope and an image from a surgical endoscope are obtained and the desired specific site is treated while monitoring the images (step S806). Then, the procedure is completed.

Here, the transfer to the on-state of the second observation functional unit is not limited to the above-described on/off state control and it may be automatically implemented after the desired part is specified in step S802.

In the fourth application example, since images from the two observation functional units of the capsule endoscope 2 can be monitored during the endoscopic surgical operation, a broader view can be obtained and securer treatment can be performed.

Next, a fifth application example will be described. In the fifth application example, a treatment is performed using only the capsule endoscope 2 and the capsule endoscope 2 is assumed to include treatment function unit for biopsy function, medication function, hemostatic function, cauterization function, marking function and the like, in addition to the observation functional unit.

Figure 66:
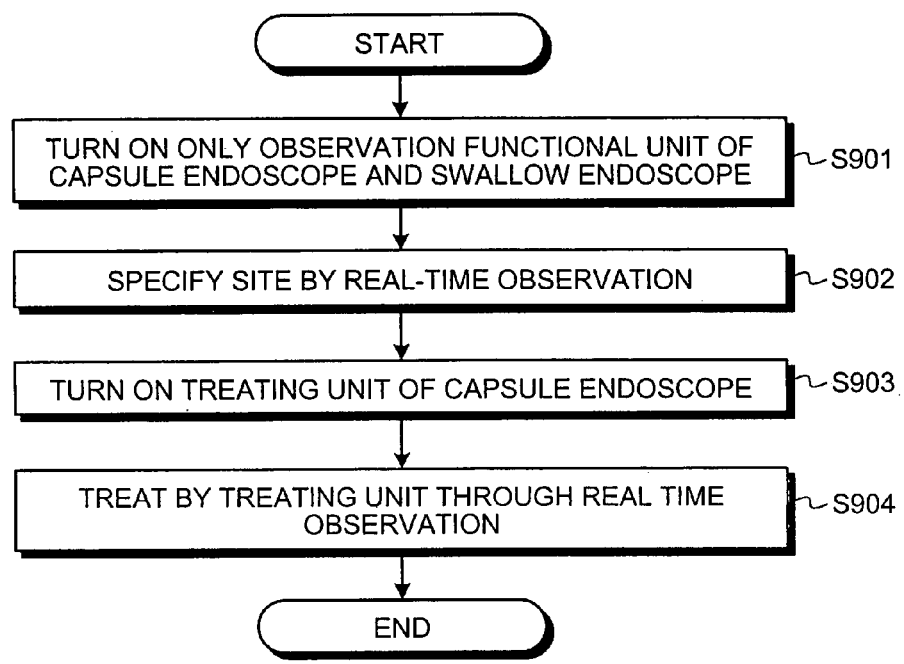
FIG. 66 is a flowchart showing a procedure of a fifth application example of the intra-subject medical system.

In the fifth application example, as shown in the flow chart in FIG. 66, firstly, only the observation functional unit of the capsule endoscope is turned on and the capsule endoscope is swallowed by a patient (step S901). Then, a desired site to be treated is specified in a real-time observation using the observation functional unit in an on-state (step S902). The treatment function unit of the capsule endoscope is turned on (step S903), and treatment is performed by the treatment function unit while performing a real-time observation (step S904). Then, the procedure is completed.

In the fifth application example, since the observation functional unit or the treatment function unit are turned on for necessary observation or treatment, the observation or treatment can be performed with minimum energy consumption.

Next, a sixth application example will be described. The sixth application example is a combination of the fifth application example and an endoscopic surgical operation.

In the sixth application example, as shown in the flow chart in FIG. 67, firstly, only the observation functional unit of the capsule endoscope is turned on and the capsule endoscope is swallowed by a patient (step S1001). A desired site to be treated is specified in a real-time observation using the observation functional unit in an on-state (step S1002). Then a locking member in the capsule endoscope is turned on to lock the capsule endoscope (step S1003). Here, in step S1003, the movement of the capsule endoscope may be stopped by administering peristalsis depressant.

The observation functional unit of the capsule endoscope is turned off (step S1004) and a preparation for an endoscopic surgical operation is performed (step S1005). When the preparation is completed, the observation functional unit of the capsule endoscope is turned on (step S1006) and the treatment function unit of the capsule endoscope is turned on (step S1007).

An image from the capsule endoscope and an image from a surgical endoscope are obtained and a treatment in association with a treatment by the capsule endoscope and a treatment by the endoscopic surgical operation is performed while monitoring the images (step S1008). Then, the procedure is completed.

In the sixth application example, treatments are performed from inside and outside of the digestive canal so that more advanced treatment can be performed.

In the above-described embodiments, an on/off state control of the body-insertable device or an on/off state control of each function in the body-insertable device is described. However, the effect of the present invention is not limited to such an on/off state control and may be applied to, for example, an operation mode switching control of each function (an input of a physical quantity triggers switching of the operation mode). For example, regarding an observing function, every time a predetermined physical quantity is applied, an observation speed (imaging flame rate) is switched from a high-speed mode used for the esophagus (e.g., 18 fps) to a medium-speed mode used for the stomach (e.g., 10 fps), and further, to a low-speed mode used for the small intestine (e.g., 2 fps). Further, regarding a medication function, operation modes for dosage, medication cycle or the like may be switched. Regarding the vital function, operation modes for amount of biopsies, cycle or the like may be switched. With this structure, operation modes of each function can be surely switched.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An intra-subject medical system comprising:
   a body-insertable device to be introduced into a subject, the body-insertable device being covered by a capsule-shaped exterior member and including:
      a physical quantity detecting member which has a directivity to detect a predetermined physical quantity;
      at least one functional member which has a necessary function for examining or treating inside the subject; and
      a switch control unit which controls an on/off state or operation mode of the at least one functional member according to a detection result of a physical quantity by the physical quantity detecting member;
   a physical quantity generator including a physical quantity emitting unit adapted to emit a temporary physical quantity inside the subject;
   a physical quantity direction changing unit which changes an emission direction of the physical quantity; and
   a control unit which controls the physical quantity emission by the physical quantity emitting unit and the direction of the physical quantity emission by the physical quantity direction changing unit,
   wherein the control unit is configured to determine whether the on/off state or operation mode of the at least one functional member is controlled by the switch control unit in response to the physical quantity emitted by the physical quantity emitting unit,
   wherein:
      when the on/off state or operation mode of the at least one functional member is not controlled by the switch control unit in response to the physical quantity emitted by the physical quantity emitting unit, the control unit changes the direction of the physical quantity emission and then performs the physical quantity emission, and
      when the on/off state or operation mode of the at least one functional member is controlled by the switch control unit in response to the physical quantity emitted by the physical quantity emitting unit, the control unit controls to stop further physical quantity emission.

2. The intra-subject medical system according to claim 1, wherein the physical quantity direction changing unit includes a mounting base adapted to mount the subject thereon, and the physical quantity direction changing unit is an emitting-unit position/posture changing unit which changes relative positions or postures of the mounting base and the physical quantity emitting unit.

3. The intra-subject medical system according to claim 2, wherein
   the physical quantity detecting member is a magnetic field detecting member for detecting a magnetic field,
   the physical quantity emitting unit is a magnetic field generating member having a magnetization direction, and
   the emitting-unit position/posture changing unit changes the relative position of the mounting base and the physical quantity emitting unit in a direction perpendicular to a magnetization direction of the magnetic field generating member.

4. The intra-subject medical system according to claim 1, wherein
   the at least one functional member is an observing member for obtaining an image inside the subject, and
   the control unit controls to turn off the observing member or switch an operation mode by emitting the physical quantity by the physical quantity emitting unit, when an image of inside of the subject sent from the body-insertable device is an image showing a desired specific site.

5. The intra-subject medical system according to claim 1, wherein the control unit controls to periodically change the physical quantity generated by the physical quantity emitting unit.

6. The intra-subject medical system according to claim 5, wherein
   the physical quantity generator further includes a movement amount detecting member for detecting a movement amount of the physical quantity emitting unit, and
   the control unit controls a period of the physical quantity corresponding to the movement amount detected by the movement amount detecting member.

7. The intra-subject medical system according to claim 4, wherein a frequency of the physical quantity which is generated by the physical quantity emitting unit and varies periodically is set smaller than a resonance frequency of the physical quantity detecting member.

8. The intra-subject medical system according to claim 1, wherein
   the control unit generates a physical quantity from the physical quantity emitting unit at a predetermined pattern, and
   when the predetermined pattern is detected, the switch control unit controls switching of the on/off states or operation mode of the at least one functional member corresponding to the predetermined pattern.

9. The intra-subject medical system according to claim 1, further comprising a position detecting member for detecting a position or a posture of the body-insertable device introduced into the subject, wherein
   the control unit controls the physical quantity emitting unit and the physical quantity direction changing unit based on the position or posture detected by the position detecting member.

10. The intra-subject medical system according to claim 9, wherein when the position of the body-insertable device detected by the position detecting member is a desired specific site, the control unit causes the physical quantity emitting unit to emit the physical quantity to turn off or switch an operation mode of the functional member.

11. The intra-subject medical system according to claim 9, wherein
   the position detecting member is a metal detector,
   the physical quantity detecting member is a magnetic sensor, the body-insertable device includes a conductive material having a surface perpendicular to a magnetism detecting direction of the magnetic sensor, and the control unit controls to emit a magnetic field in a direction parallel to a position detecting direction of the metal detector.

12. The intra-subject medical system according to claim 9, wherein the body-insertable device includes an LC marker which generates an alternate magnetic field induced by a received alternate magnetic field, and the position detecting member is adapted to be disposed near the subject, and includes a drive coil which generates an alternate magnetic field toward the LC marker and a plurality of sense coil groups which detect the alternate magnetic field generated from the LC marker, and detects the position of the body-insertable device based on arranged positions of each sense coil and a detected value of the alternate magnetic field.

13. The intra-subject medical system according to claim 1, comprising a magnetic field generating member for generating a magnetic field toward the subject in a predetermined direction, wherein the body-insertable device includes a directing member fixed therein for generating a force to move to a stable direction according to a polarity in the magnetic field in the predetermined direction; and while controlling the posture of the body-insertable device by the force of the directing member generated by the magnetic field of the magnetic field generating member, the control unit is adapted to emit a temporary physical quantity to inside the subject from the physical quantity emitting unit in a direction of a directivity of the physical quantity detecting member corresponding to the posture.

14. The intra-subject medical system according to claim 13, wherein the directing member is a permanent magnet or a ferromagnetic material.

15. The intra-subject medical system according to claim 1, wherein the physical quantity emitting unit generates a magnetic field by an electrical magnet and includes a temperature sensor, and the control unit controls power distribution time based on the temperature detected by the temperature sensor.

16. The intra-subject medical system according to claim 1, wherein the physical quantity emitting unit generates a magnetic field by a permanent magnet and, when the magnetic field is not required, the generation of the magnetic field is suppressed by a magnetism blocking unit.

17. The intra-subject medical system according to claim 16, wherein the magnetism blocking unit is a ferromagnetic material covering the permanent magnet via a nonmagnetic material.

18. The intra-subject medical system according to claim 1, wherein the physical quantity emitting unit includes a plurality of magnetic field generation sources adapted to be arranged parallel to the subject or obliquely to surround the subject.

19. The intra-subject medical system according to claim 18, wherein the plurality of magnetic field generation sources are adapted to be arranged facing each other and sandwiching the subject.

20. The intra-subject medical system according to claim 1, wherein the physical quantity is one of magnetic field, light, electromagnetic wave, corpuscular ray, sound wave, or temperature.

21. The intra-subject medical system according to claim 1, wherein the at least one functional member is at least one of an observing member for obtaining an image in the subject, a radio member for performing radio transmission of information of inside of the body-insertable device to outside the subject, a medical solution release member for releasing medical solution in the subject, a marking member for marking a desired site in the subject, a bodily fluid/tissue sampling member for sampling bodily fluid or tissue in the subject, and an operation arm member for extending and contracting the arm in the subject.

22. The intra-subject medical system according to claim 1, wherein the body-insertable device further includes:

a first functional member which has a necessary function for examining or treating inside the subject;

a second functional member which has a necessary function for examining or treating inside the subject;

a first one of the physical quantity detecting member corresponding to the first functional member; and a second one of the physical quantity detecting member corresponding to the second functional member, wherein the switch control unit controls an on/off state of the first functional member or an operation mode of the first functional member according to a detection result of the first one of the physical quantity detecting member, and controls an on/off state of the second functional member or an operation mode of the second functional member according to a detection result of the second one of the physical quantity detecting member.

23. The intra-subject medical system according to claim 22, wherein the first one of the physical quantity detecting member and the second one of the physical quantity detecting member have different receiving sensitivities.

24. The intra-subject medical system according to claim 22, wherein the first one of the physical quantity detecting member and the second one of the physical quantity detecting member have different directivities.

25. The intra-subject medical system according to claim 22, wherein the first one of the physical quantity detecting member detects a first physical quantity, and the second one of the physical quantity detecting member detects a second physical quantity, wherein the intra-subject medical system further comprises:

a first one of the physical quantity emitting unit adapted to temporarily emit the first physical quantity inside the subject;

a second one of the physical quantity emitting unit adapted to temporarily emit the second physical quantity inside the subject;

a first one a of the physical quantity direction changing unit which the emission direction of the first physical quantity; and, a second one of the physical quantity direction changing unit which changes the emission direction of the second physical quantity, wherein the control unit controls emission of the first physical quantity by the first one of the physical quantity emitting unit, controls emission of the second physical quantity by the second one of the physical quantity emitting unit, controls the emission direction of the first physical quantity by the first one of the physical quantity direction changing unit, and controls the emission direction of the second quantity by the second one of the physical quantity direction changing unit.

26. The intra-subject medical system according to claim 1, wherein the body-insertable device further includes:
a first functional member which has a necessary function for examining or treating inside the subject;
a second functional member which has a necessary function for examining or treating inside the subject;
wherein the control unit causes the physical quantity emitting unit to emit the physical quantity in a first pulse pattern corresponding to the first functional member, and to emit the physical quantity in a second pulse pattern corresponding to the second functional member, and
wherein the switch control unit controls an on/off state of the first functional member or an operation mode of the first functional member according to a detection result of the first pulse pattern of the physical quantity by the physical quantity detecting member, and controls an on/off state of the second functional member or an operation mode of the second functional member according to a detection result of the second pulse pattern of the physical quantity by the physical quantity detecting member.

\* \* \* \* \*